US011922489B2

(12) United States Patent
Chaturvedi et al.

(10) Patent No.: US 11,922,489 B2
(45) Date of Patent: Mar. 5, 2024

(54) CURATED ENVIRONMENTS FOR AUGMENTED REALITY APPLICATIONS

(71) Applicant: A9.com, Inc., Palo Alto, CA (US)

(72) Inventors: Rupa Chaturvedi, Menlo Park, CA (US); Xing Zhang, Sunnyvale, CA (US); Frank Partalis, San Francisco, CA (US); Yu Lou, Palo Alto, CA (US); Colin Jon Taylor, Orinda, CA (US); Simon Fox, Palo Alto, CA (US)

(73) Assignee: A9.com, Inc., Palo Alto, CA (US)

( * ) Notice: Subject to any disclaimer, the term of this patent is extended or adjusted under 35 U.S.C. 154(b) by 438 days.

(21) Appl. No.: 16/272,902

(22) Filed: Feb. 11, 2019

(65) Prior Publication Data

US 2020/0258144 A1 Aug. 13, 2020

(51) Int. Cl.
*G06T 19/00* (2011.01)
*G06F 3/04847* (2022.01)
*G06N 3/084* (2023.01)
*G06Q 30/0251* (2023.01)
*G06Q 30/0601* (2023.01)
*G06T 7/50* (2017.01)
*A61B 90/00* (2016.01)

(52) U.S. Cl.
CPC ..... *G06Q 30/0643* (2013.01); *G06F 3/04847* (2013.01); *G06N 3/084* (2013.01); *G06Q 30/0257* (2013.01); *G06Q 30/0633* (2013.01); *G06T 7/50* (2017.01); *G06T 19/006* (2013.01); *A61B 2090/365* (2016.02); *G06T 2207/20081* (2013.01); *G06T 2207/20084* (2013.01)

(58) Field of Classification Search
CPC ..... G06T 19/06; G06T 19/20; G06T 2210/04; G06Q 30/0643
See application file for complete search history.

(56) References Cited

U.S. PATENT DOCUMENTS 9,965,793 B1 * 5/2018 Hasan ................ G06F 16/951
2002/0010655 A1 1/2002 Kjallstrom
(Continued)

OTHER PUBLICATIONS

Non-Final Office Action issued in U.S. Appl. No. 14/853,358 dated Oct. 25, 2019.
(Continued)

*Primary Examiner* — Ryan McCulley
(74) *Attorney, Agent, or Firm* — Hogan Lovells US LLP

(57) ABSTRACT

A camera is used to capture image data of representations of a physical environment. Planes and surfaces are determined from a representation. The planes and the surfaces are analyzed using relationships there between to obtain shapes and depth information for available spaces within the physical environment. Locations of the camera with respect to the physical environment are determined. The shapes and the depth information are analyzed using a trained neural network to determine items fitting the available spaces. A live camera view is overlaid with a selection from the items to provide an augmented reality (AR) view of the physical environment from an individual location of the locations. The AR view is enabled so that a user can port to a different location than the individual location by an input received to the AR view while the selection from the items remains anchored to the individual location.

20 Claims, 16 Drawing Sheets

(56) References Cited

U.S. PATENT DOCUMENTS

| | | | |
|---|---|---|---|
| 2013/0106910 A1 | 5/2013 | Sacco | |
| 2013/0259308 A1 | 10/2013 | Klusza | |
| 2014/0267228 A1 | 9/2014 | Ofek | |
| 2014/0337175 A1 | 11/2014 | Katzin | |
| 2015/0170258 A1 | 6/2015 | Kulig | |
| 2015/0170260 A1 | 6/2015 | Lees | |
| 2016/0148433 A1* | 5/2016 | Petrovskaya | G02B 27/01 345/633 |
| 2016/0171597 A1 | 6/2016 | Todeshini | |
| 2016/0180448 A1 | 6/2016 | Ravindra | |
| 2016/0191772 A1* | 6/2016 | Jordan | H04N 5/44 348/552 |
| 2017/0287218 A1* | 10/2017 | Nuernberger | G06F 3/04845 |
| 2017/0323488 A1* | 11/2017 | Mott | G06T 19/006 |
| 2018/0143756 A1* | 5/2018 | Mildrew | G06T 19/003 |
| 2019/0012840 A1 | 1/2019 | Finman | |
| 2019/0026958 A1 | 1/2019 | Gausebeck | |
| 2019/0325653 A1* | 10/2019 | Yip | G06F 3/04883 |

OTHER PUBLICATIONS

Non-Final Office Action issued in U.S. Appl. No. 14/853,358 dated Jun. 17, 2019.
International Search Report and Written Opinion issued in PCT Application No. PCT/US19/58162 dated Jan. 21, 2020.
Satkin Scott et al: "3DNN: 3D Nearest Neighbor", International Journal of Computer Vision, Kluwer Academic Publishers, Norwell, US, vol. 111, No. 1, Jul. 22, 2014 (Jul. 22, 2014), pp. 69-97, XP035427829, ISSN: 0920-5691, DOI: 10.1007/511263-014-0734—[retrieved on Jul. 22, 2014] figures 1-3, 12, 16, 17, 30, 31 abstract, chapters 1 Introduction-3 Viewpoint Selection; p. 69-p. 76, chapter 9 Application: Geometry-Aware Object Insertion; p. 93-p. 95.
Weiss Tomer et al: "Automated Layout Synthesis and Visualization from Images of Interior or Exterior Spaces", 2017 IEEE Conference on Computer Vision and Pattern Recognition Workshops (CVPRW), IEEE, Jul. 21, 2017 (Jul. 21, 2017), pp. 41-47, XP033145755, DOI: 10.1109/CVPRW.2017.12 [retrieved on Aug. 22, 2017] figures 1, 3-6, abstract, chapters 3. Algorithm-4. Results; p. 43-p. 45.
Non-Final Office Action issued in U.S. Appl. No. 14/853,358, dated Sep. 13, 2018.
Samuel Axon, How ARKit 2 works, and why Apple is so focused on AR, Jun. 16, 2018, 8 pages.
Salsify, New Research Finds Consumers Use Mobile Devices for Product Information Whether Shopping In-Store or at Home, Apr. 5, 2017, 3 pages.
Matterport, Win more listings with 3D, Everything you need from one solution, Jan. 22, 2019, 2 pages.
Final Office Action issued in U.S. Appl. No. 14/853,358 dated Mar. 19, 2019.
International Preliminary Report on Patentability issued in PCT Application No. PCT/US19/58162 dated Aug. 10, 2021.
Non-Final Office Action issued in U.S. Appl. No. 14/853,358, dated Sep. 3, 2020.
Final Office Action issued in U.S. Appl. No. 14/853,358, dated Jun. 16, 2020.
Non-Final Office Action issued in U.S. Appl. No. 14/853,358, dated Mar. 6, 2020.

* cited by examiner

CURATED ENVIRONMENTS FOR AUGMENTED REALITY APPLICATIONS

BACKGROUND

With widespread use of computing devices, such as laptops, tablets, or smartphones, new and interesting approaches have arisen for enabling users to use these computing devices to obtain various types of information. For example, a user seeking to purchase products interacts with their electronic device, via a graphical user interface (GUI) input or other such input. The interaction may include browsing or searching through electronic catalogs for different types of products available for procurement. The user is typically unable to or not equipped to ascertain that a product or item sought for procurement would match the intended application or physical environment. In an example, the user may not be able to determine if one or more item suits the physical environment in the intended application(s); that, for instance, a table, with its size, color, or shape, would suit in a living room with a particular color of paint on its walls. Further, the user is unable to or not equipped to ascertain if items or products exist to match each other and the entirety of the physical environment. Further, such an issue is even more the case when users seek to procure expensive and dimensionally large items online because of an appreciated concern that the item might not physically and aesthetically fit into an intended space. Still further, it is often the case that such users, at the time of online purchase, may not be in the physical environment for which they are shopping.

BRIEF DESCRIPTION OF THE DRAWINGS

Various embodiments in accordance with the present disclosure will be described with reference to the drawings, in which.

DETAILED DESCRIPTION

Figure 1A:
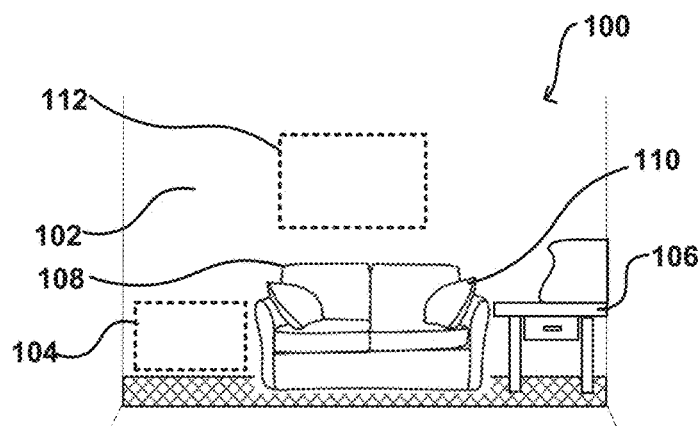
FIGS. 1A-1D illustrate a computing device used to capture a physical environment in accordance with an example of the present disclosure.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Systems and methods in accordance with various embodiments of the present disclosure overcome one or more of the above-described deficiencies and other deficiencies in conventional approaches to providing content. In particular, in various embodiments, approaches provide for curating an environment from representations of a physical environment obtained in image data provided by a camera or from other sources. The representations are obtained from the camera or from the other sources at different locations or by directing the camera in different directions in the physical environment. A floor layout may be obtained by directing the camera to the floor and walking around the floor to map its layout. Edges are marked in the floor layout to present the planes of the physical environment (separations between floor and the walls, for instance). Further planes present within the physical environment are determined from the representations by at least marking additional edges separating the planes (e.g., wall-to-wall edges). Surfaces in the physical environment are obtained by marking areas representing surfaces in the representation (e.g., table tops). The representations, including the planes, the surfaces, and the edges may be stitched or associated together to create the curated environment. The curated environment includes a three dimensional (3D) model of planes and surfaces that are available in a physical environment and may be associated to the captured images at the time of capture or at a later time. Thereafter, items may be anchored to the 3D model to one or more of the planes and/or the surfaces so that, when an augmented reality (AR) view is generated for including items in the images, the AR view shows the items as if they are anchored to the representation of the physical environment by overlaying the 3D model with the item on to the images. Image anchor points define the location and/or direction from where each representation was captured and may be used to generate the planes and surfaces, but may also be used to allow a user to traverse through the curated environment by selecting one of the image anchor points when displayed in the AR view. Selection of an image anchor point changes a displayed view in the curated environment to an associated representation that was captured from the selected anchor point. The changes, from the displayed view may be presented by a telescopic or related movement in the AR view to draw a user into the curated environment—from the displayed view to a view of the associated representation.

Alternatively, there are specific image anchor points (providing viewpoints) deemed essential, seminal, or default for the curated environment and the source providing the image data is requested to provide representations of the physical environment from these essential or default image anchor points. The curated environment may be saved as rooms or environments associated with a user or entity providing the representations in a session. Items may be added to the curated environment via augmented reality in real time or at a later time. The saved room may be accessed for adding the items. For example, in a default use case, a room may be captured (via the above-referenced representations) and viewed at a 90 degree location to at least one wall representing at least one plane, at a 60 degree angle to the wall, and a 180 degree angle to the wall. Items may be anchored to the planes and/or the surfaces in the curated environment and traversing the curated environment allows viewing of the items in the environment from the different image anchor points by keeping the items anchored in a default view from a first anchor point (e.g., 90 degree view). Further, an item in the curated environment may be moved or have its orientation changed with respect to the image anchor point of the representation. Then item-related anchor points (which may be different, same, or associated with the image anchor points) are available to fix or anchor the item to an available plane or surface (e.g., to provide different views or orientations of the item from an image anchor point) in a curated environment.

In a further aspect, an algorithm that is based in part on resolving intersections of planes and surfaces may be used to instruct or position the anchor points. Such an algorithm may start with obtaining planes and surfaces, and their associated edges; then location information of camera positions for the image(s) are obtained; coordinates in spaces may be generated to define intersections of the planes and surfaces using relative orientations of the camera and the images; the intersections are then provided as anchor points in an AR view at the time of image capture for the user. The intersections allow a user to provide a better view point for image data, to avoid certain areas because of obstructions, or to obtain clearer depth information from certain areas (e.g., corners) for item placement and to better traverse an AR view generated using the images.

The items may be associated with products provided for procurement by users through an electronic marketplace or other such electronic storefront. In response to a selection of an anchor point to view the curated environment, items or products matching the curated environment, such as being appropriate for available space in the physical environment (including decor and color of the physical environment) are provided for display in an augmented reality view with the curated environment on a computing device. A user may select to procure the displayed items or products by selecting the items or products via the augmented reality view, and may receive additional information, may save, or perform other such actions allowable in the augmented reality view.

In a further aspect, an application executing on a computing device, or remote from the computing device, can analyze the image data to determine color and/or scene information. In various embodiments, the image data can be analyzed using a trained neural network (NN), machine learning approach, or other such approach. In various embodiments, the color and/or scene information can describe a plurality of colors in the image data and can describe the room type associated with the physical environment. For example, a trained neural network may recognize corners of a table, of chairs, and of a television from the image data. The trained neural network may then conclude that the physical environment represented in the image data is a living room or may be a dining room. In response to this information and to one or more aspects selected from the representation of the room in a user device, types of items are provided to the user—either in the augmented reality (AR) view or adjacent to the AR view. In one example, selection of one or more types of items (e.g., side tables and art work) may result in one item of each types of item (e.g., a selected side table and a selected art work) to be displayed as an overlay over an image of the physical environment on a requesting computing device. The selected side table may be a closest match to available spaces and other design aspects in the physical environment. Thereafter, a user can purchase a product, save a product to a wish list or other such list, view additional information associated with the selected side table, for instance, or otherwise interact with the selected side table as described herein.

Various other functions and advantages are described and suggested below as may be provided in accordance with the various embodiments.

Figure 1B:
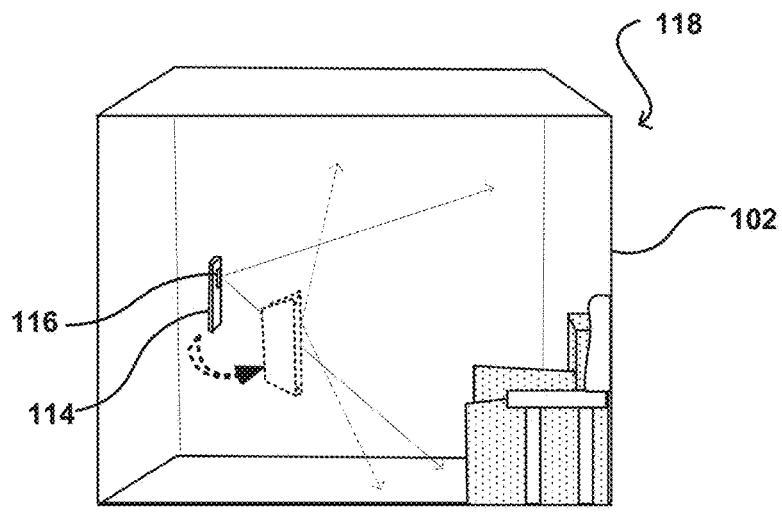

FIGS. 1A-1D illustrate a computing device 114 used to capture a physical environment 100/118 in accordance with an embodiment. In this example, computing device 114 includes a camera, such as camera 116 is illustrated in FIG. 1B. Camera 116 can capture image data (e.g., image, video, or a live camera view) of the physical environment 118. FIG. 1B illustrates a side view of physical environment 100 and that the physical environment may be captured from the present location of the camera 116 (shown by solid lines), as well as at a different location of the camera (shown by dotted lines). While shown in two dimensions (2D), a person of ordinary skill would recognize that the camera is movable in three dimensions (3Ds) to variations locations and in variations directions (at each of the various locations) to capture different representations of the physical environment—e.g., as illustrated in representations in FIGS. 1C, 1D. The physical environment 100/118 is an example of a living room with a blue color painted wall 102 and various objects, including a brown couch 108 with cushions 110, a side table 106, and areas 104, 112 for items that a user seeks to populate in the physical environment 118. Further, the camera location with respect to the physical environment is captured in the image data with the representation of the physical environment from the location illustrated in FIG. 1B. A person of ordinary skill would recognize that the areas 104, 112 are only marked for illustrative purposes to indicate areas for the items that the user seeks, and that there may be many other areas not marked but for similar purposes or that these areas are identified by the system for curating an environment, as described herein.

Figures 1C, 1D:
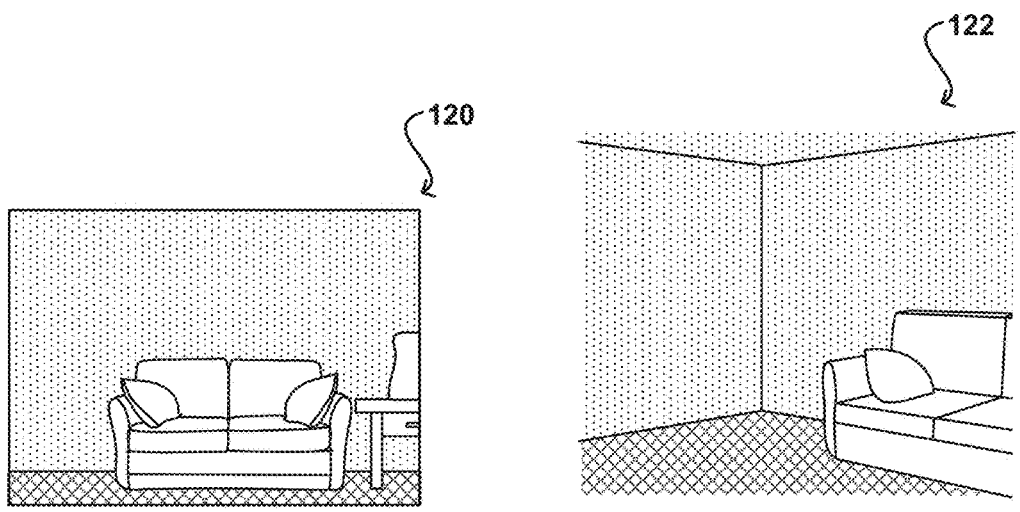

In addition, a person of ordinary skill would understand that even though reference numeral 102 is shown to a line in FIG. 1B and a general backdrop in FIG. 1A, the reference is to a wall behind the couch and that the wall (like the couch 108) may be of any color, but is presently blue (and brown, respectively) for illustrative and example purposes. FIGS. 1C and 1D illustrate live camera views, images, or video frames (reference numerals 120, 122), on a display of the computing device 116, of representations of the objects 106, 108, 110, of the wall 102, and of available areas 104, 112 from physical environment 100. The representations in FIGS. 1C and 1D are, therefore, of the physical environment as a whole. The representations of objects include corresponding color information as recognized by the camera 116 and location information for the camera during capturing of each representation. Further, the location information is stored separately from the representations. Still further, time and date information is also obtained for the representations at the time of capture.

For purposes of this disclosure, the color information, as captured in the image data of the representations of objects or items in frame 120 or 122, is considered the most accurate representation in comparison to the actual colors of the objects in the physical environment 100. The accuracy is dependent on the ability of the camera 116 to capture the full hue, tint, shade, saturation, brightness, and/or chroma of the actual color from the physical environment 100. A person of ordinary skill would recognize this and offer appropriate corrections including a notification to a user to turn on lights in the physical environment 100/118 to capture the color and light information with sufficient accuracy required to generate items with matching colors.

In an example, camera 116 comprises a digital camera incorporating a complimentary metal-oxide-semiconductor (CMOS) image sensor. In another embodiment, the camera 116 of the computing device 114 incorporates other types of image sensors, including a charged couple device (CCD), and/or can incorporate multiple cameras, including at least one wide-angle optical element (e.g., fish eye lens), that enables the camera to capture images over a wide range of angles, such as 180 degrees or more. In embodiments herein, the computing device 114 includes one or more additional cameras on the front, back, top, bottom, or sides of the computing device, and the one or more additional cameras can capture image data facing a front, back, top, bottom, or side surfaces of the computing device. Directions, such as "bottom," "top," "back," "side," and "front," are merely examples and not taken to mean specific orientations unless stated otherwise. Further, camera 116 comprises a digital still camera, configured to capture subsequent frames in rapid succession, or a video camera for capture video streams. The computing device 114, in another example, includes other types of imaging elements, such as ambient light sensors, IR sensors, other optical, imaging, lighting, or photon-type sensors.

As mentioned, a user is typically unable to or not equipped to ascertain that an item or product sought for procurement would match an intended application or the physical environment 100/118 by merely viewing the item or the product through a browser window that is isolated from at least a software image of the physical environment 100/118. Accordingly, in accordance with various embodiments, the user uses a camera of a computing device to capture more than one image, video, or live camera view of the physical environment 100/118 (e.g., from different locations in the physical environment and by different directions of the camera at a single location). This is the physical environment to which the user intends to add the item or the product. Image data from the image, the video, or the live camera view is analyzed to determine color and/or scene information forming a representation of the image, the video, or the live camera view. The color and/or scene information can be determined using one or more NNs trained to determine appropriate color information and scene information from the image data captured by a camera. Such NNs may rely on discriminant features of colors and of corners of objects in the physical environment 100/118, for instance. In an example, a trained NN determines the scene information as a room type by analyzing objects from the image data of the physical environment. When the objects are typically recognized as objects in a living room (e.g., sofa, couch, tables, lamps, etc.), the trained NN determines that the scene information includes these objects, and therefore, represents a living room. A trained NN determines colors from the color information as corresponding to colors of the various objects of the living room—including a light blue color from a painted wall or a brown color from a couch.

The image data may be an input to one or more trained neural networks, which is trained to determine colors and objects in the physical environment 100/118 to describe a type of the physical environment 100/118. In accordance with various embodiments, the type of physical environment 100/118 may include, without limitation, outdoor environments (beach, pool, apartment building, etc.), rooms in a house (living room, dining room, bathroom, etc.), context for a scene (restaurant view, a party, etc.), and related aspects that are may be readily understood to one of ordinary skill in possession of this disclosure. Accordingly, the type of physical environment 100/118 is a description to a scene or physical environment, representation(s) of which is captured by a camera. When outdoor scenery is involved, the objects are natural features of the outdoor scenery, including trees, rocks, hills, water bodies, etc.

Figure 2:
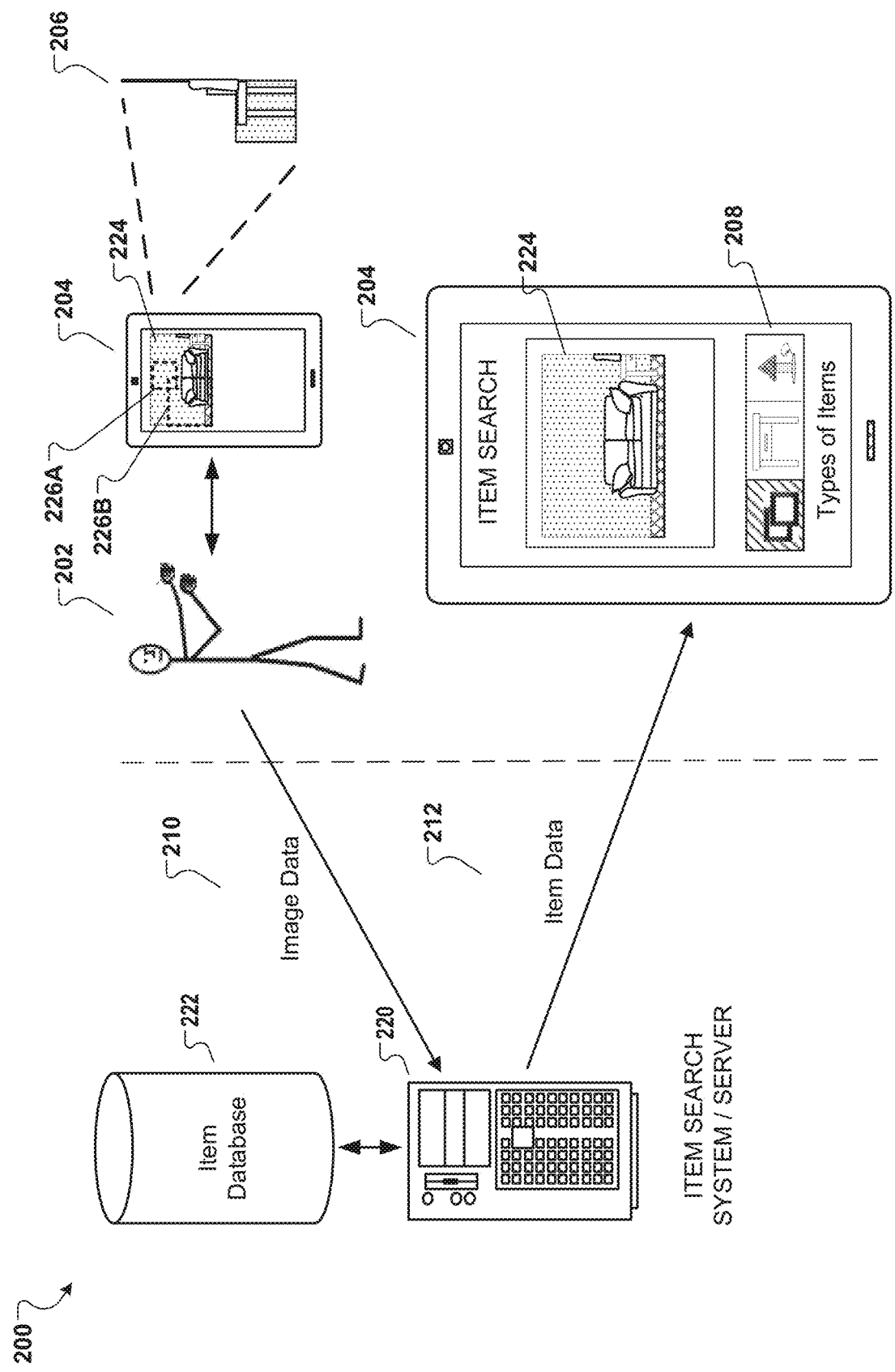
FIG. 2 illustrates an example data flow diagram of using a computing device to curate a physical environment and interacting with a product or item search system or server to obtain types of items or products for the curated environment in accordance with various embodiments.

FIG. 2 illustrates an example data flow diagram 200 of using a computing device 204 to curate a physical environment and interacting with a product or item search system or server 220, 222 to obtain types of items or products 208 for at least available spaces 226A, 226B in the curated environment in accordance with various embodiments. The types of items 208 is displayed on a display screen of the computing device 204, which may be any one of client devices 902, as described in reference to FIG. 9. In FIG. 2, a user 202 interacts with the computing device 204, through a software application executing on the computing device 204, to capture image data from a media (e.g., an image, a video frame, or a live camera view) 224, providing a representation of a physical environment 206. A person of ordinary skill would recognize that the image data may be formatted to generate the media or that media may be formed from the image data. Physical environment 206, in an example, is similar to the example living room that is physical environment 100/118 of FIG. 1A. The image data 210 from media 224 can be captured using a camera in the computing device 204. The image data includes representations of objects corresponding to objects 106, 108, 110; 210, to the wall 102, and available spaces or areas 226A, 226B from physical environment 100; 206. Additionally, in some embodiments, image data can be obtained from different sources rather than being captured by the camera of the computing device 204. For example, image data can be obtained from a different user who shared an image with the user 202, from a catalog of images, or from other third-party sources. In another example, the image data can be captured using, for example, the computing device 204 while viewing digital media, e.g., a movie, on the computing device 204.

The image data 210 includes color information in the form of the color properties from each pixel of the CCD, the CMOS, or any other applicable sensor in the camera. The color properties are best representations of one or more colors that are in the physical environment 206, to the extent of the abilities of the sensor in the camera. Such best representations may be taken as accurate representations, in an image, of actual colors from a physical environment 206. In some instances, lighting conditions that exist at the time the image 224 is captured can affect the temperature or intensity of a particular color being captured. For example, a particular shade of blue, as captured in an image, may be perceptually different if imaged on a cloudy day as opposed to being imaged on a sunny day. In aspects of the present disclosure, the user 202 can interact with the software application on the computing device 204 to select a lighting that is calibrated to the type of lighting conditions existing at the time the image 224 is being captured. For example, the user 202 can select between lighting models that are adjusted for fluorescent light, cloudy weather, sunny weather, natural light, etc. The colors captured in the image 224 can be adjusted, e.g., readjusted, in accordance to the selected lighting model.

In an example, the image data 210 is first obtained from a captured image 224. Without an ability to process the image data 210, however, the computing device 204 is unable to ascertain the representation in the image data 210. The same holds true for the scene information as well, which may also be determined from the image data 210 by further processing as described below. The image data may include color properties from relevant pixels of the image, the video, or the live camera view 224. The color properties from the relevant pixels correspond to the color information and include values for hue, tint, shade, saturation, brightness, and/or chroma for each pixel. The system of FIG. 2 may include a database 222 of items or products and may include submitted information and sponsored information as well. Further, the items themselves may be sponsored items, provided by a curator or an item sponsor, for inclusion in the augmented reality view. The items or products, in an example, may be sold directly by a provider of system 200 or may be sold from a third party that submits its inventory information of items and products to the provider of system 200. Furthermore, these existing items or products may be used, in an aspect, to train an NN comprising multiple (e.g., hidden and/or input) layers of neurons to recognize colors, objects, shapes, and dimensions, from image data. The recognized information is then used to classify new information from the image data 210 of the physical environment 206. In embodiments, multiple trained NNs or other machine learning algorithms are provided as trained to determine specific color and object information. For example, each trained NN is capable of determining a particular color value or a particular object from the general color or object information.

In this example, the user 202 interacts with the computing device 204, through a software application executing on the computing device 204 to select one or more portions 226A, 226B of the image 224 for determining spatial information (e.g., dimensions), color information, and scene information as to the portions 226A, 226B. The portions 226A, 226B, may represent available spaces in the physical environment for new or replacement items. Thereafter, the types of items 208 may be provided as item data 212, based on the portion(s) 226A, 226B of the image 224, and related items or products may be subsequently provided based in part on a selection of one or more types of items from the types of items 208. This is further illustrated in FIG. 3. Accordingly, this example illustrates processing of the one or more portion(s) 226A, 226B (from one or more different locations or directions of the camera) in the image data 210, instead of the whole image data from the image 224. Alternatively, the image data 210 provided to the server 220 may be the selected the one or more portion(s) 226A, 226B (from one or more different locations or directions of the camera) of the image 224, instead of image data of the whole image 224. This process improves response times in view of reduced data transfer which reduces latency with the amount of data 210, 212 transferring to and from the server 220 and the amount of processing that occurs in the server 220. Relative information (e.g., location of the camera and its direction) between the camera and the features of the room as provided by users may be obtained during image capture and may be mapped to pixels of each representation (or image) in a JSON file. For example, information to pixel-level representation of features (e.g., planes, surfaces, and other standard features) with respect to the direction and location of the camera in the physical environment may be stored in the JSON file as a mapping.

Further, in an aspect, a portion of the image 226 may be selected by using a zoom mode associated with the display for the image. This may be after the image 224 is captured, or associated with the camera of the computing device, or during capture of the image 224. When the zoom mode is used during capture, more features and clarity is obtained to help the system identify objects, available space, and colors. Particularly, the item data 210 is more focused or more defined in its scene and/or color information as the camera pixels of the computing device 204 are exposed to specific and non-variant light inputs reflecting from a reduced area in the physical environment than when an exposure occurs without the zoom mode. The image data captured with the zoom mode provide the scene and/or color information with a degree of separation of objects and of colors from the physical environment that is better than plainly using the entire image data, without the zoom mode. The degree of separation may be measured by the distance between differently colored pixels, for instance.

For object detection, corners or lines are clearer as the focus is on a limited space. In doing so, the software is able to compensate for the zoom as to actual measurement of scale for determining scene features such as dimensions of available areas for items in the physical environment. In an example, an initial calibration is performed by capturing an image or an AR view of a physical ruler with dimension markings placed against a fixed backdrop with at least two markings to provide relative calibration to a virtual ruler for future use. Alternatively, a virtual ruler may be lined up with the physical ruler and the camera moved to a position where the markings on both rulers coincide. Thereafter distance (including the addition of zoom) automatically compensates the virtual ruler based in part on the calibration. When the zoom mode is used on the image after the image is captured, more colors and scene information may be defined in the image data as the displayed pixels are more granularly separated to reveal slight color variations with more clarity than the image 224 without the zoom mode. As in the case of the zoom mode during capture, the granularly separated pixels is separated by a degree of separation measured by the distance between the pixels. Accordingly, in an example, as the zoom occurs, the types of items (or even the items associated with the types of items) may change to reflect new spaces and/or colors contained in the granular pixels of the zoomed portion of the image.

In some embodiments, International Standards Organization (ISO) settings for measuring sensitivity to light can be used to automatically adjust color settings. For example, a camera may automatically adjust its ISO settings depending on lighting conditions that were determined by a light sensor in the camera. A lower ISO setting can indicate high lighting conditions while a higher ISO setting can indicate low lighting conditions. This observation can be used by, for example, the software application executing on the computing device 204 to adjust the color settings so that the colors in the captured image are visually similar to colors that were actually perceived by the user 202.

Once the image 224 has been captured, the computing device 204 can either use the image as a whole or extract a patch, e.g., a patch of pixels, from the image 224 for capturing color. Furthermore, one or more different representations, from the image 224, may be used to correlate the captured color as different directions of the camera or different locations of the camera may return colors influenced by the physical environment in different ways. The pixels of the whole image or the patch provide the basis from which scene and color information in the image 224 is identified. The patch may be associated with the portions 226A, 226B. Alternatively, the patch may be automatically extracted based in part on areas that are without color variations (indicating possibly empty areas which may be suitable for new items). When a patch is used, the patch can be defined as a fixed width and height, e.g., 100 pixels by 100 pixels. As noted in some aspects, the user 202 can interact with a display screen of the computing device 204 to manually define the portion or region, e.g., a circular or rectangular portion 226A, 226B, in the image 224 from which scene and/or color information may be identified. The region can be defined using, for example, a stylus or a finger—by creating a bounding box around the region of interest.

Extracting a patch from the image 224 can also allow for identification of a spectrum of colors that are present in the image 224 or in the patch of image 224. Further, user 202 may seek to use colors from one portion 226B of image 224 (including one representation associated with one location or direction of capture by a camera) to identify a similarly colored item for a different portion 226A of the image 224. In doing so, influence(s) from the physical environment to part of the image 224 from other directions and locations will not affect the colors appreciated by the user. In an alternative aspect, color and scene information is used to provide types of items 208 and to provide color options to further filter the types of items 208.

In aspects, the user 202 can interact with a display screen of the computing device 204 to identify a single color, e.g., using an eyedropper tool, that identifies a pixel in the image 224. Thus, for example, for an image that includes multiple colors, the user 202 can still select a particular color in the image. In some situations, the user 202 may not be satisfied with the colors in the captured image. A color temperature slider may be provided, along with an aspect filter (e.g., filter 486 in FIG. 4E), on the display screen of the computing device 204. In such an aspect, the user 202 can interact with the color temperature slider to adjust the temperature of the captured colors, without having to take a second image of the physical environment from the same direction or location, or without having to adjust the native camera hardware and software of the computing device 204. The aspect filter may also be used to adjust initial aspects of the representative of the physical environment so that the items of one or more types of items are further narrowed to the requirements of the aspect filter.

In an example, the scene may be a singular representation of information that includes relative spatial coordinates for sub-representations of objects that are typical to a room type. The determination of the scene information from an image of a physical environment may provide determination of the room type associated with the physical environment. For example, a living room may typically include a couch, a television, side tables, and other features. A kitchen will typically include an island, a stove, a microwave, utensils, etc. Feature determination or recognition using relative coordinate system or specific features of representations of objects is applicable in training one or more neural networks to perform identification for the room type.

One or more neural networks may be trained to use the scene information of relative spatial coordinates for representations of objects to recognize or determine objects from subsequent images and to use that object recognition to describe the room type as a living room or a kitchen. In an example, the scene information may include grouped values of coordinates or other recognizable feature variations to describe representations of objects. In an example, the system herein utilizes a relative coordinate system from the time of image capture or after image capture to provide relative measurements for predetermined points in the representation of objects of the physical environment. Such points may be referred to herein as points of interests. A couch may have a fixed structure defined by a plurality of related coordinate points. A table might have a different set of related coordinate points. Moreover, the points of interests may also be used across images captured at a later time, with secondary considerations of location, to determine if a new image (including a representation of a physical environment) is related to a prior image. Such relationship information is then used as part of curating an environment for the physical environment and to allow traversing the curated environment from the prior image to the new image via telescoping, pivoting, or other such traversing processing.

In an example, telescoping refers to blurring features between the prior image and the new image while keeping an image anchor point in clear view while moving a user interface from a view of the prior image to a view of the new image at the image anchor point. The image anchor point is generally used interchangeably with anchor point and is used herein to refer to a point in an image (and associated representation) or in a physical environment from which another image (and associated representation) or an image for the representation is captured. The image anchor point is different from an item-related anchor point, which is a point on an item added to a 3D model of the curated environment. Further, in an aspect, the item may only be added to the 3D model when the 3D model is overlaid to the representation. However, it is possible to add items to the 3D model, where the items present its own 3D component to associate with the 3D model prior to being overlaid on the representation. A person of ordinary skill reading the present disclosure can differentiate the image anchor point and the item-related anchor point taking the context of each disclosed embodiment. The related coordinate points between objects may, therefore, be relative to a point of image capture, reflecting the anchor point, or to an arbitrarily chosen point in the image after it has been captured. The arbitrary chosen point may be an offset from the actual point at which an image is captured. This may be done to prevent blocking of important viewpoints in an augmented reality view applied to the representations. An example neural network that is trained to recognize each of the related coordinate points for multiple object representations can then distinguish a room type in a physical environment using the objects in the physical environment. The pivoting feature allows the prior image to be associated with the new image by at least one spatial point shared between the two images. Then movement from the prior image to the new image pivots the prior image by a blurring or other image transformation to the new image.

In the previously described example of a living room, the color information may include variations of blue and brown colors—the blue color from the wall and the brown color from the couch. Upon determination of available space in the representation, for instance, an overlay may be provided with items or products associated with the room type and with the available space, in the live camera view or in the curated environment. For example, the items or the products may include a brown (e.g., wood) side-table suited to the space and an alternate option that is less preferably for the living room. The overlay in the live camera view or in the curated environment provides an augmented reality view of the physical environment.

The product search system or server 220 provides item data 212 to the computing device 204. To identify visually similar colors, the product search system or server 220 can compare the color information that was received from the computing device 204 with respective color information from various color samples of a content, product, or training database. In some embodiments, the color samples correspond to colors that have been determined to be popular colors. Further, the item listing may also be provided in accordance with other popularity measures—such as based in part on sales of the item or recent media coverage of the item. In an embodiment, the color samples correspond to sponsored colors that have been selected by a curator or an item sponsor for inclusion in the types of items.

In an example, the process of generating or providing visually similar colors for the type of items 208 (and subsequently for the items), as part of an image processing step, is based on providing visual similarity scores for the colors from the image data. In an example, first color values are associated to a plurality of colors in a database 222. Such values may be arbitrary, but different for each and every variation of color. Second color values are associated to pixels providing the image data from a physical environment. The image data can include pixel properties that provide, in an example, color information for the image of the physical environment. The second color values form the color information. The example then uses a comparison of each of the second color values to each of the first color values to provide the visual similarity scores the second color values. In an example, a standard assignment process is used to assign color values in a manner that is consistent for the type of camera sensor used. In a further example, the above similarly measure process is used with an NN to teach one or more NNs to recognize or determine colors differences and to assign a pixel color as a part or within a family of a known color in a more efficient manner than visual recognition alone. Such NNs may rely on minute variations—that are typically difficult to ascertain with a human eye—in pixel properties to find any difference in hue, tint, shade, saturation, brightness, and/or chroma of a color, and to better classify the color in accordance with known colors from color samples in the database 222.

In another example, the process of generating or providing visually similar colors for the type of items 208 (and subsequently for the items) may be based in part on color samples with a score that satisfies a color threshold value (for known colors) in measure of similarity with other colors in the image data. The color threshold value is applicable as a basis to train one or more NNs to recognize or ignore fine color differences. For example, when the color threshold value for a particular color is low, an implication may be that high similarity must exist for a color from the image data to classify as a color associated with the color threshold value. When the color threshold value for a particular color is high, low similarity may exist, and colors from the image data with larger differences in their color properties as against the color properties (reflected in the color threshold value) of the particular color are still classified as represented by that particular color. This may be the case to restrict the threshold value for particular colors (base colors, for instance). In restricting the threshold value for a particular color, a trained neural network may be trained to limit colors with only slight variations from the average values for hue, tint, shade, saturation, brightness, and/or chroma of that particular color. Thus, in the prior example involving blue color walls in a living room, the types of items and subsequent items provided to computing device 204 may include one or more colors that are visually similar to the particular color of blue recognized from the image 224 of the living room 206. The user 202 operating the computing device 204 can select a color, either as an initial aspect from the live camera view or as an aspect filter from a sliding filter after a first (or initial) list of items is provided. When the sliding filter is used, a response may be provided from the server 202 to update the first list of times.

In yet another example, the process of generating or providing types of items or items with visually similar colors from the image data may be based in part on using a global histogram of color representatives for pixels of the image data. The global histogram represents a distribution of color in an image or a patch of the image. For example, representations of objects in an image include different colors and a histogram of the different colors, over a number of color representatives, forms the color information of the image data. The product search system or server 220 determines a color family histogram for at least a portion of the pixels of the image data. Colors for the color family histogram are determined from the properties of pixels in the image and can be mapped to one or more color representatives and color families associated with the color family histogram. The product search system or server 220 determines color information for the image by normalizing and combining (or concatenating) the global histogram with the color family histogram. The color information can be scaled to have a unit Euclidean norm. A weighting factor can be applied to the color family histogram or the color representative histogram. In some embodiments, the color family histogram is weighted by a factor, e.g., 1.0, 1.1, or 1.2. The normalized and combined (or concatenated) values are then applied as training values to an NN for training the NN to distinguish colors. The weighting factor may be applied as the training weights for the NN.

In yet another aspect, the process of generating or providing the types of items or items with visually similar colors from the image data may be based in part on processing color distances from image data of pixels. The image data is compared with known color information from the database 222 using distance measurements. Such distance measurements include dot product, cross product, and Euclidean distance, in a color space, to provide a visual similarity score. Such product or distance information is then applicable to train or teach an NN to recognize similar differences and to classify pixel colors. Color samples from a database 222 that satisfy a threshold visual similarity score, as established using products or distance information, can be selected as a color that is visually similar to a color described by the provided color information for the image. As a result, the selected color samples from the database 222 can be included in the types of items or in subsequent items under the types of items. Thus, the types of items or the items themselves include one or more colors that are visually similar to a color in the extracted patch of the captured image. Furthermore, when distance measurements form the basis for color classification or distinction then the above referenced NN may be taught to recognize colors differences in accordance with distance limits and may use such teachings to assign a pixel color as a part or within a family of a known color.

In some embodiments, the color samples from which visually similar colors are identified are restricted to popular colors. For example, when identifying colors that are visually similar to colors in the extracted patch, the product search system or sever 220 only evaluates colors that have been determined to be popular. Popular colors may be colors that are associated with certain items, e.g., items or products that have been identified as being popular for a particular physical environment. For example, a blue color for a living room can be identified as a popular color based on an evaluation of sales data for products, e.g., tables, art work, lamps, curtains, rugs, wall decor, etc., that each have that same blue color in them. In another example, the popular color is the predominant color of the item or the product. In this example, a blue lamp with orange markings is included in the provided results for the color and the physical environment. Evaluating sales data to identify a popular product can include determining whether the item or the product satisfies a threshold sales volume or threshold revenue. Items or products that are in demand for a physical environment, e.g., trending, can also be identified as being popular.

Popular colors and items can also be segmented, for example, based on types of items, which may also represent a product category for a physical environment. In an aspect of such an application, based on an evaluation of sales data for products in different product categories, a color orange can be identified as a popular color for products in the rugs category, but not for products in a curtains category. In some embodiments, the color samples from which visually similar colors are identified corresponding to curated colors that have been manually selected by an entity, e.g., individual, business, or organization. For example, a curator or item sponsor is a third party provider (see reference 906 in FIG. 9) that can select one or more colors, as sponsored colors, that are in fashion for a particular time period. The sponsored colors can correspond to a particular brand of products. For example, a particular shade of blue that is being used in the spring curtain collection for a particular brand can be identified. When the particular shade of blue is visually similar to a color that is in the extracted patch of an image, then that particular shade of blue can be included in the types of items or the items themselves that are presented to the user 202, thereby priming the user to possibly select a curated product.

In such an implementation for priming the user for products via the present disclosure, a determination is made for a first color value of color information of an image that satisfies a threshold value and is associated with first items from items available for the physical environment. Scene information, as described throughout this disclosure, provides relevant information to support mining of the items associated with the physical environment. A determination is made for a second color value of the color information of the image that satisfies the threshold value and that is associated with a second product of the available products for the physical environment. The present system and method may, however provide, as part of the types of items or the items themselves, and in a predetermined order, a first and a second colors associated with the first and the second color values respectively. Pertinently, the present system and method provides the first and the second colors as part of the types of items or the items themselves in a manner to prime the selection of the first color ahead of the second color. For example, the first color is displayed, as part of the types of items or the items themselves, in a higher numerical order or in bigger display area of the user interface including the AR view. Alternatively, the first color is displayed with the higher numerical order or in the bigger display area of the AR view. Furthermore, the first color is displayed first, followed by the second color. This example process would cause the user 202 to select the first color with higher probability than the second color, thereby causing a potential sale of the corresponding first product over the second product. The above examples, with respect to color sponsorship, are also available to other aspects of the representation of the physical environment—e.g., to sizing (sponsorship to rank large appliances that gross higher profit margins over smaller appliances), to material (sponsorship to rank leather and higher quality materials over lower cost or inferior materials), etc.

Figure 3A:
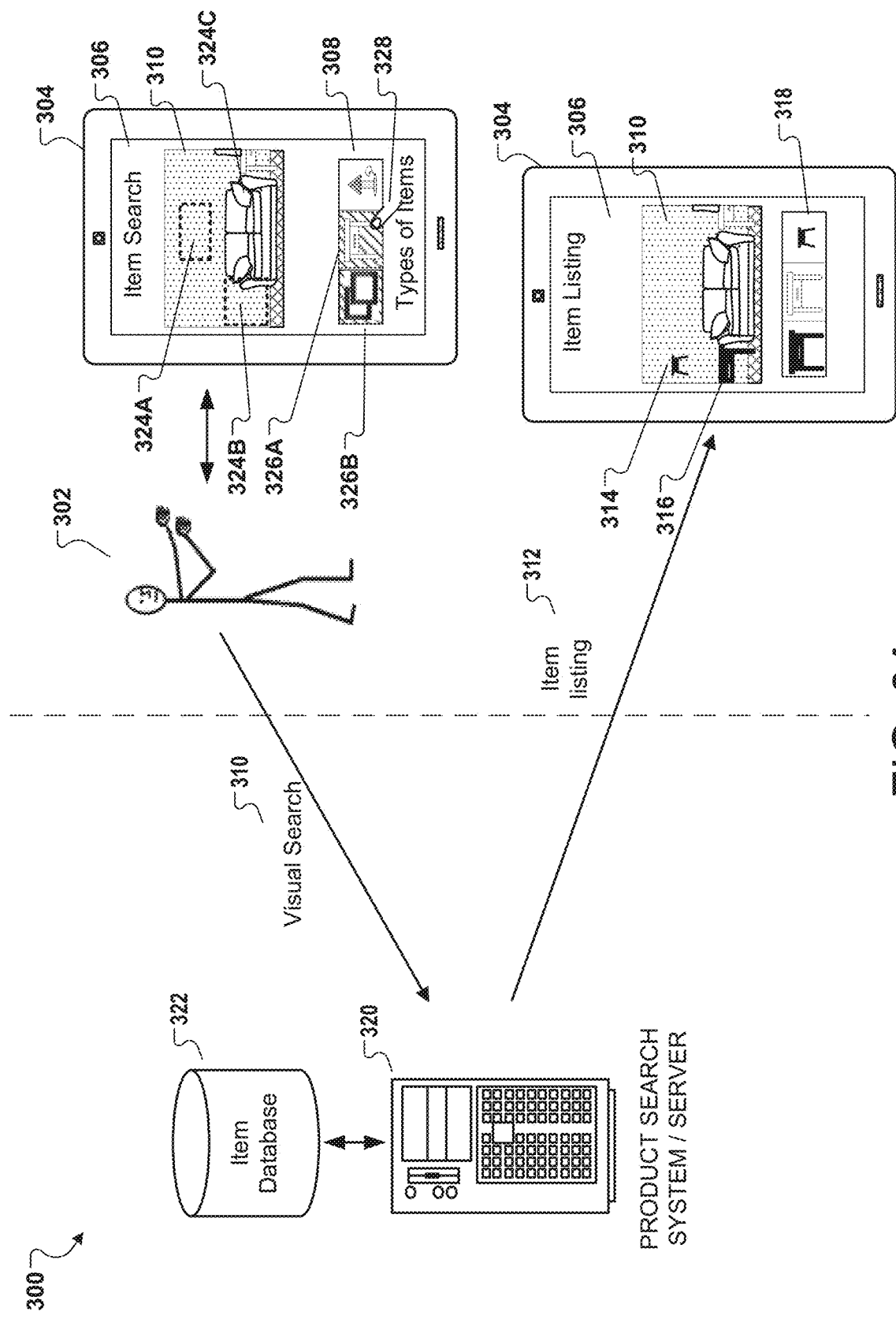
FIG. 3A illustrates a further example data flow diagram of using a computing device to curate a physical environment and interacting with a product or item search system or server to select from the types of items or products for the curated environment in accordance with various embodiments.

FIG. 3A illustrates a further example data flow diagram 300 of using a computing device 304 to curate a physical environment and interacting with a product or item search system or server 320 to select from the types of items or products of an item or product database 322 for the curated environment in accordance with various embodiments. The data flow of FIG. 3 may follow after the data flow of FIG. 2 is complete or after a part of the data flow of FIG. 2 is complete.

In an example, the image data from an image, a video, or a live camera view of a physical environment, is provided as input to a trained NN that is able to determine scene information, color information, and other information capable of being used as aspects from the image data. The scene information, as previously noted, may describe objects that are typical to a room type, and therefore, determines a room type associated with the physical environment. Alternatively, the trained NN determines the scene information by recognition of unique spatial coordinates of available spaces or prior items associated with representations of objects in the image data or calculated from the image data. Furthermore, planes and/or surfaces are determined from the image data for the physical environment. The planes and the surfaces define walls, ceilings, floors, table tops, and other areas where new or replacements may fit in the representation, and therefore, in the physical environment—once procured. An example of this process is discussed with reference to FIG. 6 in this disclosure.

From a trained NN analysis of scene information, the sever 320 is configured to recognize one or more of the representations of objects from the image data as part of a database of known rooms. When the trained NN identifies a couch and a table, for instance, in the scene information of the image data, the trained NN can provide an indication that the physical environment captured in the image data is a living room or a study area. When the trained NN identifies a sink and a tub in an image of a physical environment, for instance, the trained NN may then indicate that the room in the physical environment is a bathroom. In effect the trained NN for the scene information may work in two stages—first, to determine the scene information as to the objects in the physical environment from comparison of features to those in a scene information part of a database 322, and second, to determine that the collective scene information describe a known type of room based on a comparison of features to those in a room type portion of the database 322.

The computing device 304 displays the types of items 308 on a display screen 306 of the computing device 304. The user 302 can use any interaction tool 328 to interact with the computing device 304 for selection 326A, 326B of one or more types of items, as previously described. In addition, the user 302 can also interact with the computing device 304 to select or define aspects for an intended item. Such aspects may include a selection of a spatial area for placement of the item, e.g., one or more regions 324A, 324B. The system will be able to use the previously detailed AR measurement features to scale the spatial area and to consider items (with the selected one or more types of items) to fit those spaces. In the alternative or together with the spatial area aspect, the user 302 may also be able to select a color or material aspect by selecting the couch 324C (or part thereof) for referencing a color, material, or any other feature (associated with the couch) to be the color or the material aspect associated with the intended item for inclusion in the live camera view. Further, the spatial area aspect may also be referred to herein as a dimensions aspect. Other aspects available to the user include weight, color, shape, texture, material, and size. The size aspect may be a generalized form of the dimensions aspect, which may be more specific—e.g., including exact measurements. The aspects may also be defined by textual or numerical input. For example, the dimensions aspect and the weight aspect may be provided in typed in values. Alternatively, for the weight aspect, when the couch is selected for the system to determine its own aspect, the system may be able to generate items (e.g., side tables) that were previously purchased by customers who bought similar style couches. The recognition here is that customers who purchased specific other items to go with a similarly styled couch would do so based on aspects associated with the couch. For example, one such aspect may include weight, where a customer of the similarly styled couch would have an expectation of certain weight limits to other furniture they may purchase with the couch.

The selected or the determined aspects and the selected types of items may be provided as a visual search 310 to system/server 320 for analysis and determination of items or products that are associated with these two features. The items or the products may be first determined from stored information with relationship tags for each type of item in the types of items. The relationship tags associate each of the item or the products with one or more types of items. The items or the products are then matched to the selected or the determined aspects. The order of identification of the items or the products may be reversed—first to the types of items and then the aspects—in an implementation. In either implementation, the items or the products may be filtered to a best match (e.g., an item matching as many of the selected or the determined aspects ranks the item at the top or places the item in prominence in the overlay for the AR view). In an example, when generating the items or product, the product search system 320 can further modify an order in which items are provided in the item listing 312. The item listing 318 displayed on display 306 of computing device 304 may be then presented in a separate area of the display 306.

One or more items 316, 314 may be overlaid in the live camera view or in the curated environment to provide an AR view 310 of the physical environment. For example, in some embodiments, the product search system or server 320 can evaluate aspects that are associated with products preferred by a user or are generally used most often by the user, e.g., color aspects, dimension aspect, or products previously purchased by the user. The history of the user's interest in product, browsing history, preferences, products placed in the user's shopping cart, products flagged by the user as being of interest to identify colors, dimensions, weights, and other aspects, may also be used to anticipate and prepare the system to respond with appropriately ordered items. This reduces latency and improves response times for the system, thereby making the AR experience as smooth as possible. In embodiments, when the user captures an image that contains a color or shape that is visually similar to one of the user's preferred colors or shapes, for example, then the preferred color or shape can be ordered in the item listing before other colors or shapes are included. This may be relevant for identifying art work, for instance, for placement in the physical space represented by region 324A. In an aspect, the user can manually specify one or more preferred colors or any of the other aspect via typed input, as previously noted. This overrides the system's determinations from historical data or from the image data. As used in this specification, ordering an item with a specific typed aspect before a second item involves positioning, in the item listing, of the first item in a position that comes before, e.g., to the left of, the position of the second item.

Figure 3B:
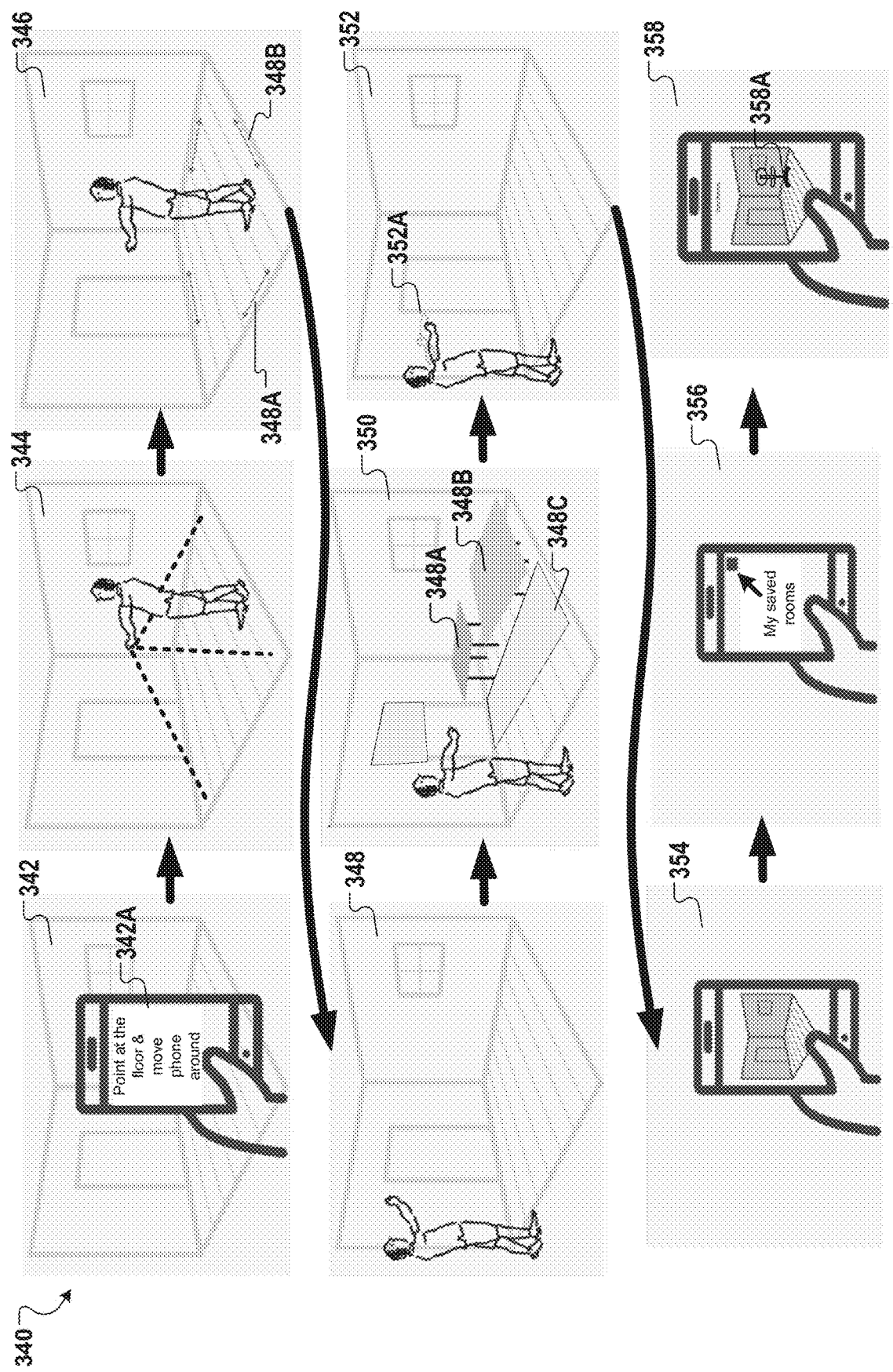
FIG. 3B illustrates an example data flow diagram of using a computing device to curate a physical environment from a user's perspective in accordance with various embodiments.

FIG. 3B illustrates an example data flow diagram 340 of using a computing device to curate a physical environment from a user's perspective in accordance with various embodiments. The example of FIG. 3B may occur at the time of image data capture, as illustrated via FIG. 2. In an example, at illustrative 342, a computing device 342A informs a user to point a camera of the computing device 342A to the floor and to move it around so as to be able to capture a floor plan or layout for the physical environment (illustrated as a room). As previously noted, relative information of the layout with respect to the camera is obtained and stored in a JSON file for each representation captured by the camera. In an example, the floor plan or layout may be used for verification of the planes—e.g., the walls and relative location of the walls. Moreover, the walls may be used in an orthogonal projection to generate a floor layout or plan view of the physical environment. As such, many of the steps discussed herein may be performed in different sequences and a person of ordinary skill would recognize this from the disclosure herein. At illustrative 344, the computing device 342A is illustrated as being pointed to the floor as the used navigates the physical environment. In an embodiment, if a wide angle lens is used, the required movement of the camera may be minimal. Furthermore, the location and time of image capture at each location, if the computing device is being moved, is noted and tagged or otherwise associated with the image data being captured. Illustrative 346 shows that edges are marked in the representation obtained in the computing device 342A. In an example, the user may be provided with a prompt to provide edges between physical structures (e.g., presently walls to the floors) or such edges is determined (and may be confirmed via user intervention) using one or more neural networks trained to identify edges by such discriminatory variables as shadows between the physical structures. In an example, the ceiling may be used instead of the floors in illustratives 342, 344.

Illustrative 348 follows illustrative 346 and shows the computing device 342A being used to capture walls and other physical structures, following which edges are marked between these physical structures using similar methods as with respect to the walls to the floors in the prior illustratives. The walls and the ceiling may be referred to as planes. The computing device 342A is then used to determine surfaces (e.g., 348A, 348B, and 348C), via illustrative 350, where items may be settled upon. In a further example, illustrative 352 shows that the user may be requested to change the direction of the camera while capturing addition image data (associated with representations) of the physical environment. In an aspect, a person of ordinary skill would recognize that the planes and surfaces may be stored using relative coordinate information—e.g., the relative distance (as marked by coordinates at the corners of each of the planes and the surfaces) from the corners to other corners and to the location at which each image was captured (image anchor points). Such information allows generation of the 3D model of a curated environment that can separate the planes and surfaces as solid flat areas that may be then overlaid to the physical environment to create the curated environment. The 3D model may be solid flat areas may be transparent in the overlay and may be used to anchor items, which then appear anchored in the representation of the physical environment. While the table surfaces 348A, 348B are not illustrated in the remaining illustratives 352-358, a person of ordinary skill would recognize that they may exist if in actual application of the present disclosure.

Further, the planes and surfaces forming a 3D model may be stored in a singular file with the image data or maybe stored in a filed separately associated with the image data. However, when an AR view of an image associated with the image data is requested, the 3D model may be overlaid on a representation of a physical environment form the image. Traversing the image to reach a second image associated with the image data will result in the 3D model being traversed to show another view of the planes and surfaces from a different viewpoint or anchor point associated with the second image. Then an item anchored in the 3D model is visible from a different orientation than the orientation when anchored in the 3D model. In a further example, the planes and surfaces may be toggled ON and OFF to clear space in the AR view for ease of use. This may be by toggling ON and OFF the 3D model while maintaining the representation in a display on the computing device. Such an effect may be also achieved by turning ON and OFF the AR view associated with the representation in the display. The computing device 342A includes an orientation sensor (e.g., 1110 of FIG. 11) to provide orientation information along with location (also via element 1110 of FIG. 11) for the image data captured at each change of the direction asserted to the camera.

Illustrative 354 follows from illustrative 352 and shows that the end result of the image data collected via illustratives 342-352 is a 3D representation of the physical environment and the planes and surfaces in the physical environment. As such, image data may be continuously collected and sent to the server for processing using steps previously discussed to track movement, orientation, and/or points of interests between each frame or image of the image data. In an aspect of the disclosure, the 3D representation of the physical environment may be taken to include the 3D model of the planes and surfaces generated by the processes and systems of this disclosure. A person of ordinary skill would understand, based on the disclosure herein, that reference to the 3D representation then also refers to the 3D model of the planes and surfaces associated with the representation, unless expressly indicated otherwise. This cumulative information results in the representation that is stitched together or associated in the manner illustrated in illustrative 354. The 3D representation may be used in real time or may be stored, as in illustrative 356. The stored 3D representation may be accessed at a later time to add items for previewing prior to procurement. In a further example, the stored 3D representation may be further augmented by additional image data that is associated or stitched to the prior 3D representation after matching orientation, location, and points of interests between the additional image data and the stored 3D representation. In an example, the association maintains time difference information between the stored 3D representations and the additional image data, such that a view of the representation may be provided at two different times. As such, this process allows items (e.g., chair 358A added to the 3D representation in illustrative 358) to be added in one view representing a first time, and then viewed in a second view representing a second time. Light reflection changes occurring as a result of the views captured in different times provide more accurate and real interfacing of an augmented reality interface to the user. In addition, movement from the first view to the second view, even if in the same location and orientation, may be by a telescoping movement that telescopes between the views by focusing at the center of the view and blurring between the first view till the second view is completely shown and the first view is overwritten.

Figure 4A:
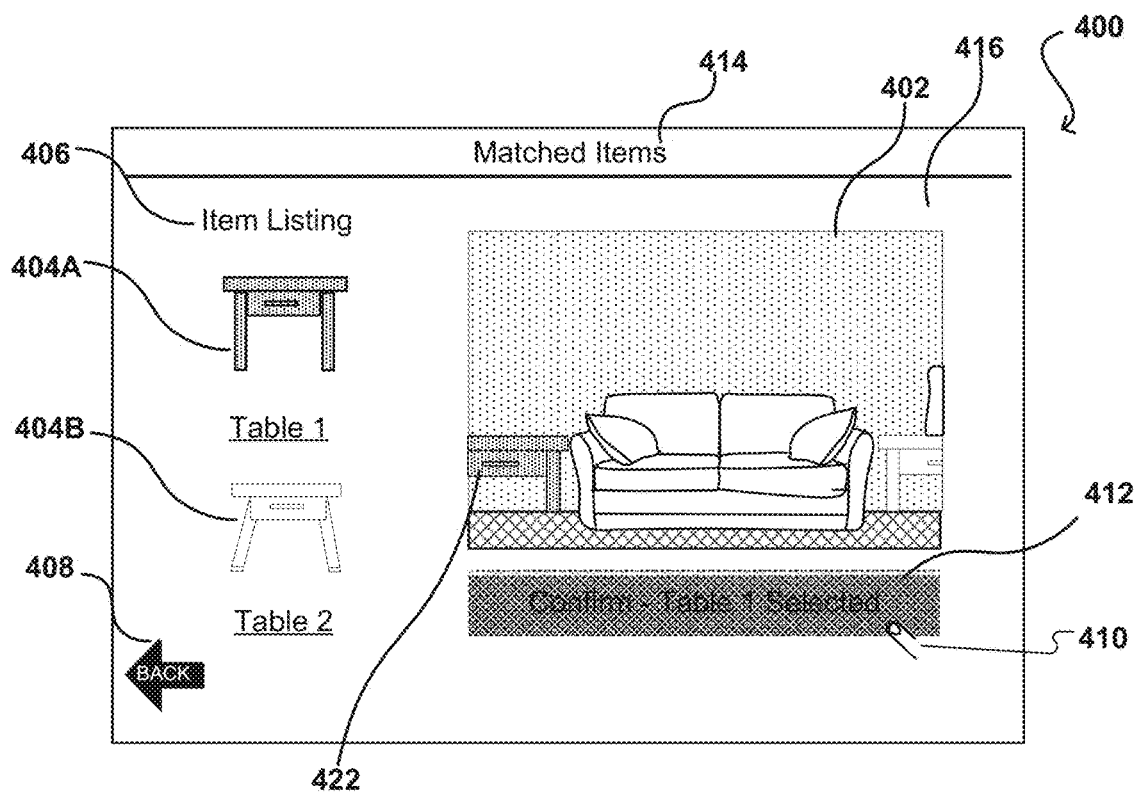
FIGS. 4A-4B illustrate example user interfaces for augmenting a curated environment of a physical environment represented in an image, video, or live camera view with an item associated with one or more types of items suitable for the curated environment in accordance with various embodiments.
Figure 4B:
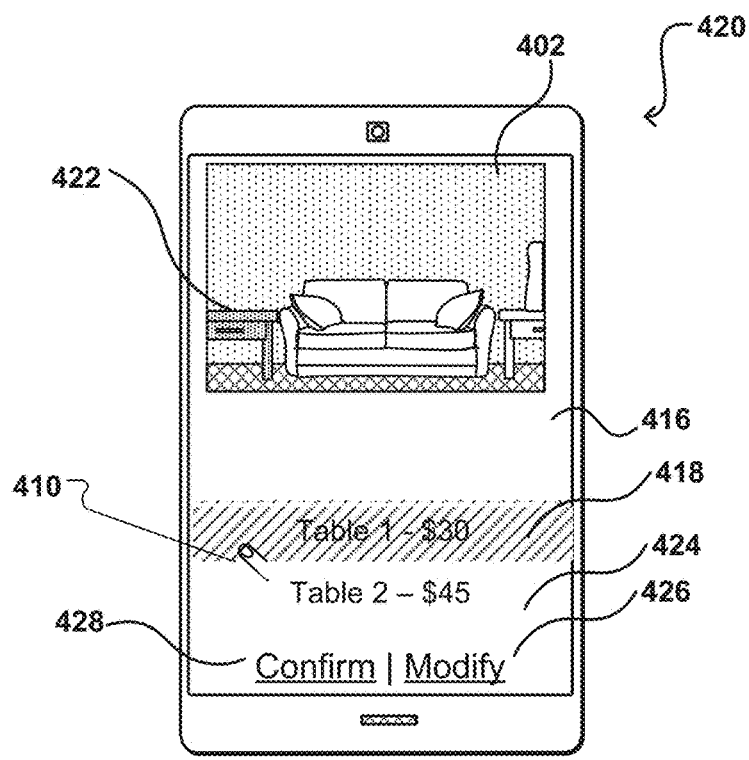

FIGS. 4A-4B illustrate example user interfaces for augmenting a curated environment of a physical environment represented in an image, video, or live camera view with an item associated with one or more types of items suitable for the curated environment in accordance with various embodiments. FIG. 4A illustrates an example UI 400 on a computing device, such as the computing devices in FIGS. 2-3B and described throughout this disclosure. UI 400 may follow the UIs of FIGS. 2-3B (see example UIs on the computing device 204 of FIG. 2). UIs are generally used herein to describe the look, feel, and information communicated to a user for user interaction in an AR view of the curated environment using aspects determined from image data of a live camera view. The aspects may be determined by user selection in the live camera view, by manual input to the UI, or by the use of the trained NNs to determine that available spaces exist to add items (or to replace available items depending on the type of the physical environment) using the image data. The UI 400 is titled Matched Item 414 to provide the user with information in the AR view 402 in UI area 406 of Item Listing the best matched item. For example, AR view 402 includes item 422 as in the case of FIG. 3A. In addition, UI area adjacent to the AR view 402 provides item listing of the same item 404A and other relevant items (e.g., item 406) for placement within the AR view 402. In an alternate implementation, there is no Item Listing and the AR view 402 may include items 404B and 422, both overlaid in the live camera view or curated environment, with item 404B floating in the AR view, and item 422 fixed to the available space in the live camera view or curated environment.

When the user selects an item or product 404A, 404B; 422, from the AR view 402 or from the Item Listing area, the product or the item 404A, 422 is highlighted in both, the AR view 402 and the Item Listing area 406. A person or ordinary skill would recognize that the items 442A, 442B are at least displayed in the overlay in its original color and without disruptions to provide the clearest display of the AR view prior to any highlighting. The highlighting may occur after the user has completed reviewing the fit of the item(s) to the physical environment via the AR view 402. An input via an input feature 410 in area 412 confirms the selection of the item 422 provided by the user. In an aspect of the disclosure, even though alternate item 404B is not a best match, the user may move the item 404B over to the space where the best match item 404A is presently illustrated. This causes the best match item 404A to move out of the space to a free area (or previous area of the alternate item 404B), and causes the alternate item 404B to be displayed in the space as an updated overlay to the live camera view or curated environment. In an aspect, as the alternate item 422B is unsuited by its dimensions to the space, the overlay may not accept the user's attempt to move the alternative item 404B to the space. In a further aspect, the alternate item 404B may be moved to the space, but further information may be displayed that dimensions (of the item or the space) need to be changed. This may be by subtracting the item's dimensions from the space's dimensions. This information may be provided in a red or other distracting marker to clearly illustrate conflict of the item to the space available. The marker for conflict is merely used in this example for illustrative purposes if a conflict should occur, but for the remainder of the example assumes that the item 404A is a best match to the area adjacent to the couch, and that its placement in the area is a visible marker of the best match.

The table's position or selection may be modified using a finger or stylus 410 or other gesture recognition process to select clickable or selectable area 412. When moveable, a highlight or bounding box appears over the item 404A, 404B and it may be moved using the same finger, stylus 410, or gesture, to another area in the UI 416. Alternatively there is no special highlighting or bounding box and the items 404A, 404B are always movable to cause the overlay to refresh with the AR view 402 showing the items in the desired positions once the movement has ceased. A BACK button 408 allows the user to reset choices by revisiting the prior UI screen to select different aspects or types of items. The item 422 may be anchored or fixed to the back wall of the representation illustrated in AR view 402. The item 422 may include a marker opposite to an item-related anchor point on its body. The marker is visible to the user and informs the user that the item 422 may be fixed or anchored to any plane or surface in the curated environment by its item-related anchor point (typically opposite surface to the marker, but may be located elsewhere on the item relative to the marker). Moreover, the curated environment may allow items fixed to all its planes or surfaces, but may alternatively mark certain areas for anchoring items and may restrict other areas of the representation. Such a decision may be by user preference provided in the curated environment during definition of the edges, the planes, and the surfaces, for instance.

The UI 416 in FIG. 4B may be a subsequent UI from the UI 400, on the computing device 420 hosting the UI. The UI 416 includes the AR view 402 of the curated environment with the selected item 422 overlaid for procurement. After the user has decided on the item 422 as the item of choice for procurement, the UI 416 in FIG. 4B provides options 418, 424, 426 to begin the purchase or procurement of the selected item 422. Alternatively, information about the item or advertisement associated with the item is provided during display of the item for procurement, in a subsequent UI, or in an overlay to the AR view 402 of the UI 416. Procurement options for the product, in an example, include costs 418, 424 for each of the selected item 422; 404A and the unselected item 404B. In addition, the current or a subsequent UI portion may be scripted to provide availability information for renting or leasing the item. The user is provided with the pricing available for each of the items 418, 424, and may use a finger or other input 410 to select to confirm purchase at the listed price. Confirm or modify options 426, 428 provide verification prior to confirming purchase.

Figure 4C:
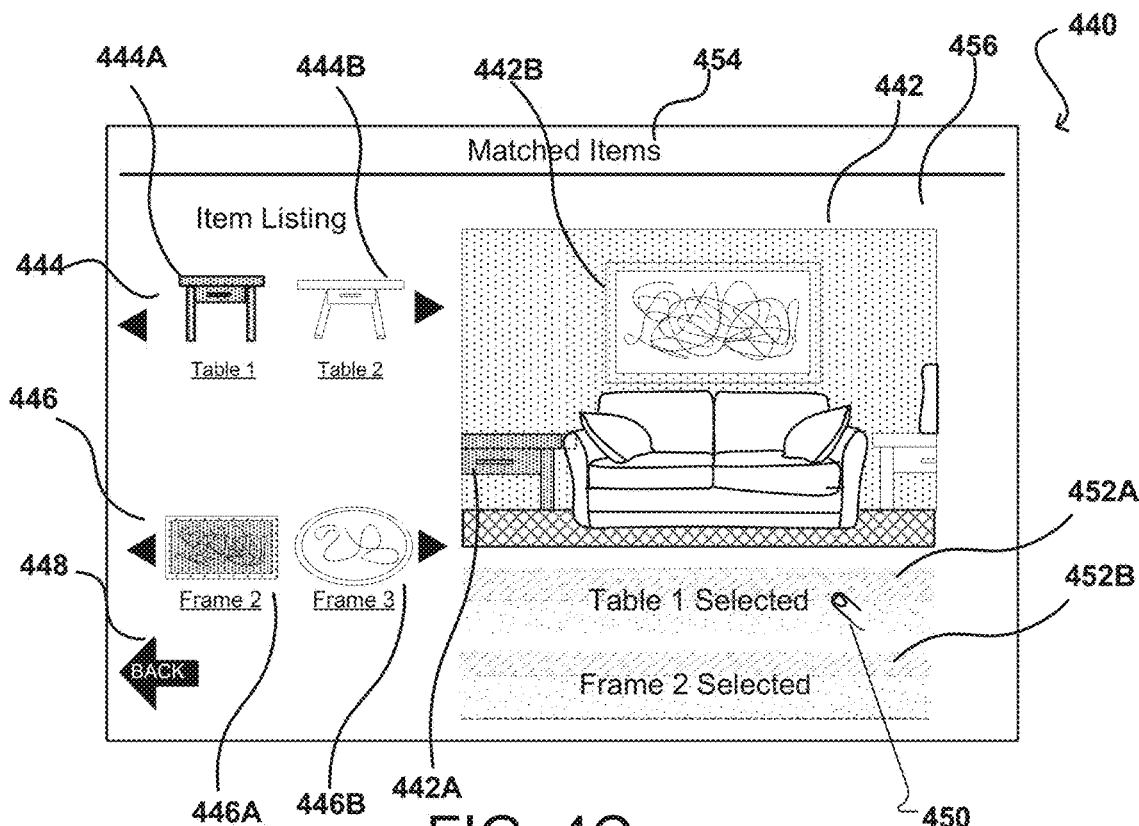
FIGS. 4C-4D illustrate example user interfaces for augmenting a curated environment of a physical environment represented in an image, video, or live camera view with multiple items associated suitable to each other and for the curated environment in accordance with various embodiments.
Figure 4D:
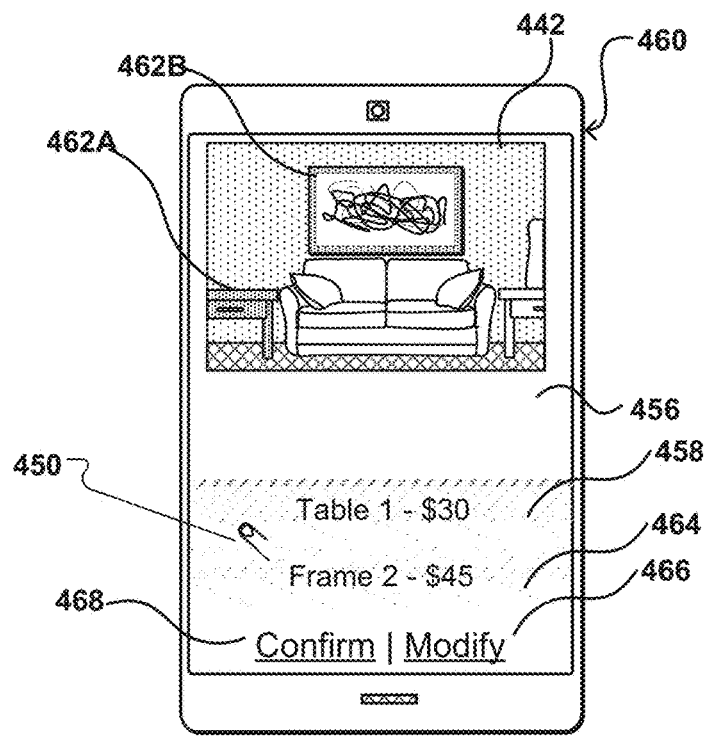

FIGS. 4C-4D illustrate example user interfaces for augmenting a curated environment of a physical environment represented in an image, video, or live camera view with multiple items associated suitable to each other and for the curated environment in accordance with various embodiments. FIG. 4C illustrates an example UI 440 on a computing device, such as the computing devices in FIGS. 2, 3A, 3B, and 4B, and as described throughout this disclosure. The UI 440 may be an alternate interface to the UI 400. The UI 440 may also follow the UIs of FIG. 2 (see example UIs on the computing device 204 of FIG. 2) and may be displayed instead of UI 400. The UI 440 is titled Matched Items 454 to provide the user with information in the AR view 442 in UI areas 444, 456 of the best matched items. Here, unlike UI 400, two items 442A, 442B, from two different types of items (Frames and Tables) are matched and overlaid for the AR view 442. For example, AR view 442 includes the two items 442A, 442B. Additional or alternate items may not be populated to the AR view 442 to avoid crowding the AR view 442. However, these items 444A, 444B, 446A, 446B may be provided in appropriate UI areas 444, 446 that are adjacent to the AR view 402. In an alternate implementation, there is no Item Listing and the AR view 402, with the items 442A, 442B, overlaid in the live camera view or the curated environment is provided in the UI 440.

When the user selects the items or products 442A, 442B, from the AR view 442 or from the Item Listing area, the products or the items 442A, 442B may be highlighted in both, the AR view 442 and the Item Listing area. A person or ordinary skill would recognize that the items 442A, 442B are at least displayed in the overlay in its original color and without disruptions to provide the clearest display of the AR view prior to any highlighting. The highlighting may occur after the user has completed reviewing the fit of the item(s) to the physical environment via the AR view 442. Input via an input feature 450 in areas 452A, 452B confirm the selection of the items 442A, 442B provided by the user. In an aspect of the disclosure, even though alternate item 444B, 446B are not best matches, the user may move one or more of these items over to any space already occupied by the best match items. This causes the best match items to move out of the space to a free area (or previous area of the alternate item(s)), and causes the alternate item to be displayed in the space as an updated overlay to the live camera view. In an aspect, as one or more of the alternate items are unsuited by its dimensions to the space, the overlay may not accept the user's attempt to move either of the alternative items to the space. In a further aspect, the alternate items may be moved to the space, but the markers may include further information that dimensions (of the item or the space) need to be changed. This may be by subtracting the item's dimensions from the space's dimensions. This information may be provided in a red or other distracting marker to clearly illustrate conflict of the item to the space available.

The table's position or selection may be modified using a finger or stylus 450, or other gesture recognition process to select clickable or selectable areas 452A, 452B. When moveable, a highlight or bounding box appears over the item 442A, 442B and it may be moved using the same finger, stylus 450, or gesture, to another area in the image 442. Alternatively there is no special highlighting or bounding box and the items 442A, 442B are always movable to cause the overlay to refresh with the AR view 442 showing the items in the desired positions once the movement has ceased. A BACK button 448 allows the user to reset choices by revisiting the prior UI screen to select different aspects or types of items.

The UI 456 in FIG. 4D may be a subsequent UI from the UI 440, on the computing device 460 hosting the UI. The UI 456 includes the AR view 442 with the selected items 462A, 462B for procurement. After the user has decided on the items 462A, 462B as the items of choice for procurement, the UI 456 in FIG. 4D provides options 458, 466 to begin the purchase or procurement of the selected items 462A, 462B. Additional prices and clickable areas for procurement may be shown once the screen is scrolled. Alternatively, information about the items or advertisements associated with the items may be provided during display of the items for procurement, in a subsequent UI, or in an overlay to the AR view 442 of the UI 456. Procurement options for the product, in an example, include costs 458, 464 for each of the selected item 462A, 462B and the unselected item 444B, 446B. In addition, the current or a subsequent UI portion may be scripted to provide availability information for renting or leasing the item. The user is provided with the pricing available for each of the items 462A, 462B, and may use a finger or other input 450 to select to confirm purchase at the listed price. The confirm or modify options 466, 468 provide verification prior to confirming purchase.

Figure 4E:
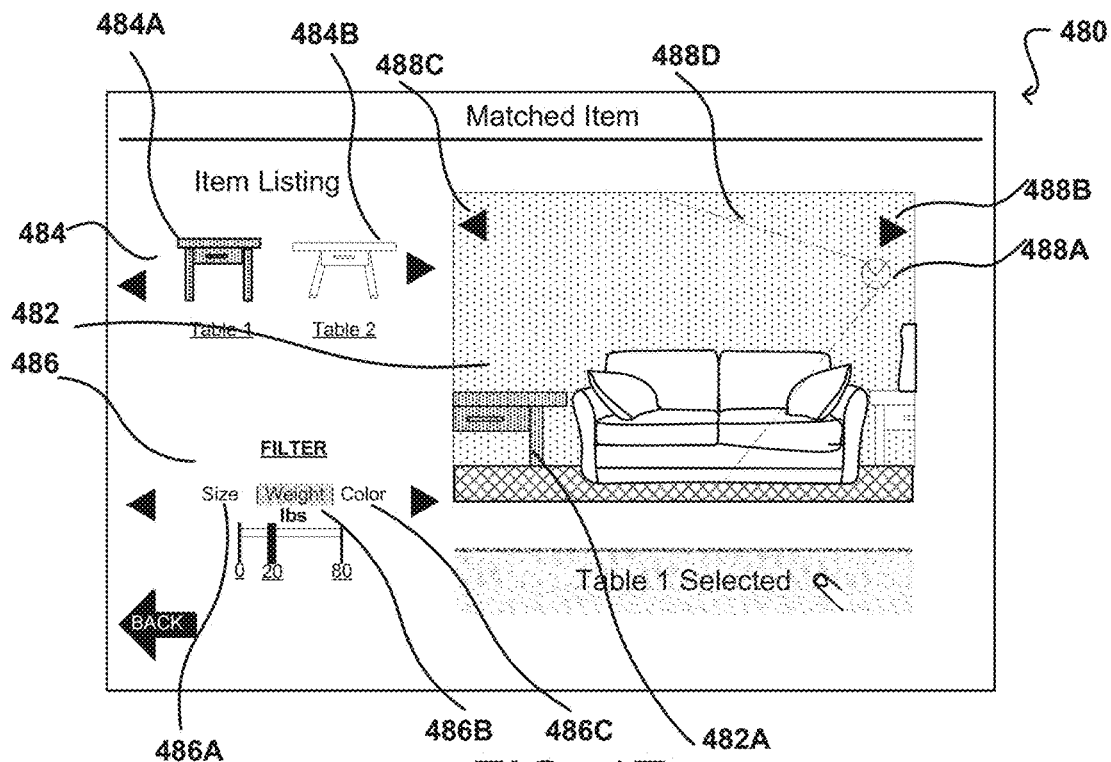
FIG. 4E illustrates an example user interfaces for traversing a curated environment of a physical environment represented in an image, video, or live camera view and inserting an item via augmented reality in the curated environment in accordance with various embodiments.

FIG. 4E illustrates an example user interface 480 for traversing a curated environment of a physical environment represented in an image, video, or live camera view and inserting an item 482 via augmented reality in the curated environment in accordance with various embodiments. UI 480 may follow the UIs of FIG. 2 (see example UIs on the computing device 204 of FIG. 2). The UI 480 is titled Matched Item to provide the user with information in the AR view 482 of the best matched item. For example, AR view 482 includes item 482A. In addition, UI area adjacent to the AR view 482 provides Item Listing of the items available for insertion within the AR view 482 and may include a slider filter 486 to further filter the items available by various aspects. The slide filter 486 provides fine tuning to the various aspects 486A-C, including dimensions, colors, etc., determined to generate the at least two items 484A, 484B. However, the slide filter 486 may also be used to add additional aspects to further filter the items in the Item Listing. In such a case, the items may be all stored in a buffer of a client device hosting the UI 480 and may be filtered on the client side for faster and smoother AR viewing experience. However, it is also possible to load new items based on input from a server to remove (or add) certain items to the AR view 482 after the filter is applied. While the slide filter is provided as an example, any other applicable software filter may be used to provide suitable UI experience to the user.

The position or placement of item 482A represents a best fit for the available space in the curated environment. A floating area may be a designated dock in an overlay applied to the live camera view or the curated environment. As such, the placement of item 482A in an area desired or intended for the item implies that it is a best match to the physical environment and the aspect(s) chosen by a user or applied from a neural network learning of the physical environment—e.g., the space available, the colors in the physical environment, the shapes of other items in the physical environment, or the relationship between items of different types selected for the physical environment. In an example, markers 488A-C are provided to allow traversing of the curated environment to determine that the best fit is indeed the case for item 482A.

Figure 4F:
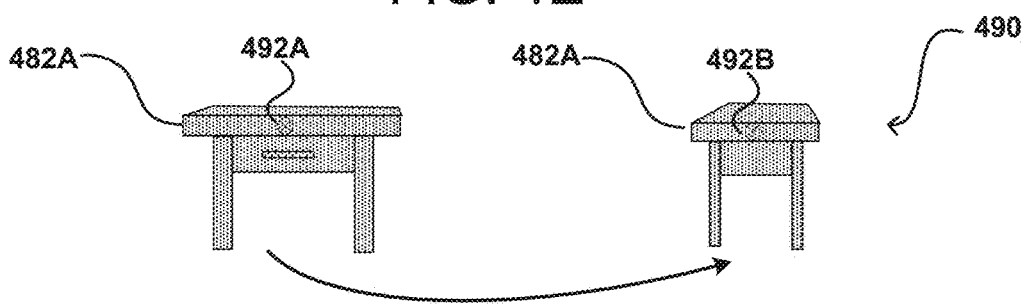
FIG. 4F illustrates an example of an item having markers associated with an anchor point for fixing the item to a plane or surface of the curated environment.
Figure 4G:
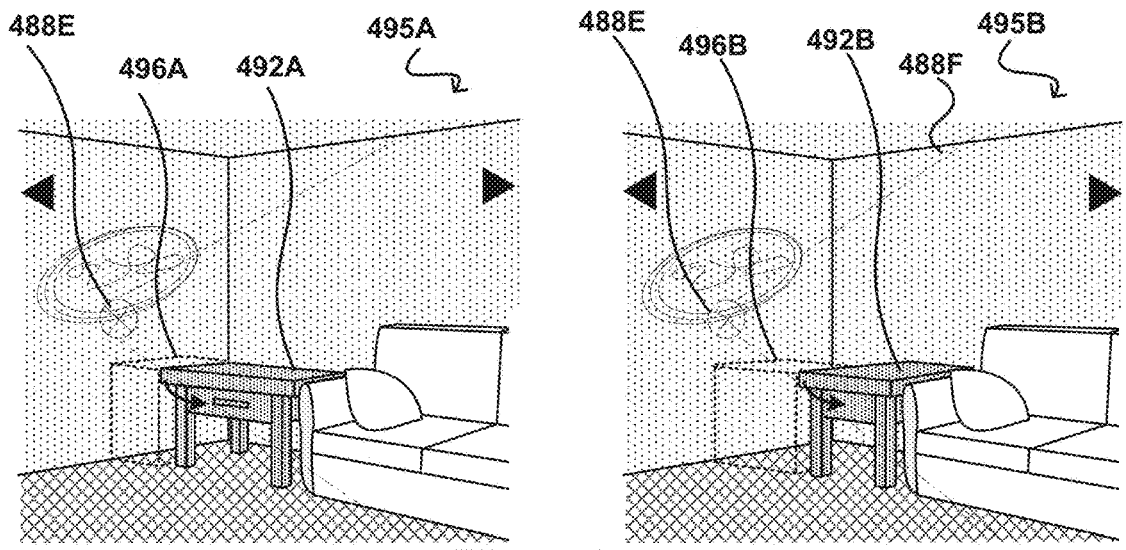
FIG. 4G illustrates an example traversal through a curated environment by selection of markers in the curate environment in accordance with various embodiments.

As such, even though item 482A is placed in an intended area of the live camera view or the curated environment versus another item, e.g., item 484B, which may be placed in a random or floating location in the AR view, a user may traverse the curated environment to see another view of the item 482A in the area shown in FIG. 4E. For example, selection of markers 488A-C changes the AR view to a representation of the physical environment that was captured from a physical point (in the physical environment) represented by at least marker 488A. Such a representation is provided in the example illustrations of FIG. 4G. In an example, the item 482A is anchored by an anchor point (opposite to the spot marked 492A in FIG. 4F) to the plane (i.e., wall) behind the couch. As such, the selection of the marker 488A may change the AR view to the view in FIG. 4G, but the item 482A remains as disposed in the area with its back portion anchored to the wall behind the couch. A different view of the item is thus provided (and marked under reference numeral 492A to reflect a different view but the item is the same item 482A). The user can now see that space 496A is available for further items or for a larger table. This was not initially possible by a single view as in FIG. 4E. The curated environment, by its multiple views stitched or associated in the manner of the present disclosure, allows multiple viewpoints to the physical environment from the representations, but also allows for traversing of the representations and the AR view with an inserted item anchored to one or more planes or surfaces. In the example of FIGS. 4E, 4G, the item 482A is fixed or anchored to the plane of the wall behind the couch, and separately, to the surface of the floor.

In a further aspect, illustrations 490, 495A, 495B show that a user may rotate the item 482A (FIG. 4F and 4G), such that at least one of the item's shorter sides now is anchored or fixed to the plane of the wall behind the couch. Markers 492A, 492B indicate that an opposite side of the item 482A is available for anchoring to a plane or surface in the curated environment. The user is now able to see more available space 496B in configuration 495B than in configuration 495A. As in the case of FIG. 4E, markers or representation anchor points 488A, 488E and arrows (e.g., 488B, 488C) are provided to move between representations in the curated environment. For example, selecting marker 488E allows the user to go back to the viewing angle of FIG. 4E. Selecting arrows 488B, 488C goes to any next available representation.

In a further implementation, the angle of the anchor point to the plane in FIG. 4E (also the angle at which a camera or source capture the representation) is 90 degress to the plane of the wall behind the couch, while the angle of the camera or source of the representations in FIG. 4G is 60 degrees to the plane of the wall behind the couch. These may be preferred angles or anchor points for obtaining the representations to curate the environment. These may also represent essential or default anchor points for viewing or capturing representations to curate the environment. Further, while anchor point is used for both the items and the curated environment, context is provided in each case and a person of ordinary skill would recognize what is under discussion based in part on the context. For example, markers 492A, 492B are used to illustrate that anchor points exist in an opposite surface and allow the item 482A to be anchored to a plane or a surface in the curated environment by the anchor points. However, anchor points 488E and 488A are used to refer to points from which a view of a representation is available in the curated environment (or to points from which the representation was captured by a camera or from a source providing the representation). In addition, dotted lines or other highlighting methods 488D, 488F may be applicable to illustrate to a user the area captured from a particular anchor point 488A, 488E. A person or ordinary skill would recognize that clicking on an unmarked area in the AR view would remove the annotations of the markers 488A-D from the AR view to provide clear viewing of the item 482A inserted into the curated environment; and a further clicking of the unmarked area in the AR view could bring back the annotations for easy toggling between information provided and the plain AR view.

In a further aspect, the dashed box 496A, 496B may be a virtual aspect added to the live camera view or the curated environment to support the AR view of the physical environment. The dashed box 496A, 496B is only an example marker, and other types, shapes, graphics, text, or variation may be used instead. The dashed box may be also generated to fit into the available space with at least a dimension that matches existing (and added virtual) items in the physical environment or the curated environment. For example, the dashed box 496A, 496B is generated to a height that is a maximum (or average or other statistical unit) of height of an existing item (e.g., couch) or added virtual item 492A, 492B. In this aspect, it is also possible to place an item that fully fits into the space as a best match, but when that item is replaced by a smaller item previously floated in the AR view, the smaller item may invite generation of a dashed box or other visible marker to the area remaining in the physical environment adjacent to or related to the space where the smaller item now fits.

In a further example, the dashed box 496A, 496B, along with the other virtual items (and/or visible markers) 488A-F, are fully selectable or clickable. In essence, a user may provide input (touch, click, gesture, or in any other manner) to the dashed box 496A, 496B or the other virtual items or markers 488A-F, and relevant item is selected. Furthermore, instead of a selection or with the selection, a pop-up may be presented with menu items applicable to the relevant item under selection. The pop-up may alternatively provide a listing of options within the AR view. The relevant item 484A; 482A under selection may be indicated by a highlight, a graphic, a color, or a change to a visible marker already provided to the relevant item. Still further, as discussed elsewhere in this disclosure, the dashed box 496A, 496B may alternatively indicate an overlap or conflict of the item with other objects in the physical environment. As in the case of the discussion throughout this disclosure, the dashed box 496A, 496B may be of other properties for visual distinction (e.g., a graphic indicator, a color indicator, text indicator, etc.). Any of these visual distinctions serve as a visible marker that applies for illustrating overlap or conflict based on any of the discussed aspects, including dimensions, shapes, colors, etc.

The filter 486 is illustrated as including aspects such as size 486A, weight (presently selected to demonstrate a usage) 486B, and color 486C. When the user selects an item or product 484A, from the AR view or from the Item Listing area, the product or the item 482A is highlighted in both, the AR view and the Item Listing area. A person or ordinary skill would recognize that the items 484A, 484B may be at least displayed in the overlay in its original color and without disruptions to provide the clearest display of the AR view prior to any highlighting. The highlighting may occur after the user has completed reviewing the fit of the item(s) to the physical environment via the AR view. An input via an input feature (similar to the prior examples of FIGS. 4A, 4C) confirms the selection of the item 482A provided by the user. In an aspect of the disclosure, even though alternate item 484B is not a best match, the user may move the item over to the space where the best match item 482A is presently illustrated. This causes the best match item 482A to move out of the space to a free area (or previous area of the alternate item), and causes the alternate item 484B to be displayed in the space as an updated overlay to the curated environment. In an aspect, as the alternate item 484B is unsuited by its dimensions to the space, the overlay may not accept the user's attempt to move the alternative item 484B to the space. In a further aspect, the alternate item 484B may be moved to the space, but the markers may include further information that dimensions (of the item or the space) need to be changed. This may be by subtracting the item's dimensions from the space's dimensions. This information may be provided in a red or other distracting marker to clearly illustrate conflict of the item to the space available.

The table's position or selection may be modified using a finger or stylus or other gesture recognition process to select clickable or selectable area. When moveable, a highlight or bounding box appears over the item 484A, 484B and it may be moved using the same finger, stylus, or gesture, to another area in the AR view. Alternatively there is no special highlighting or bounding box and the items 484A, 484B are always movable to cause the overlay to refresh with the AR view showing the items in the desired positions once the movement has ceased. A BACK button allows the user to reset choices by revisiting the prior UI screen to select different aspects or types of items.

Figure 5A:
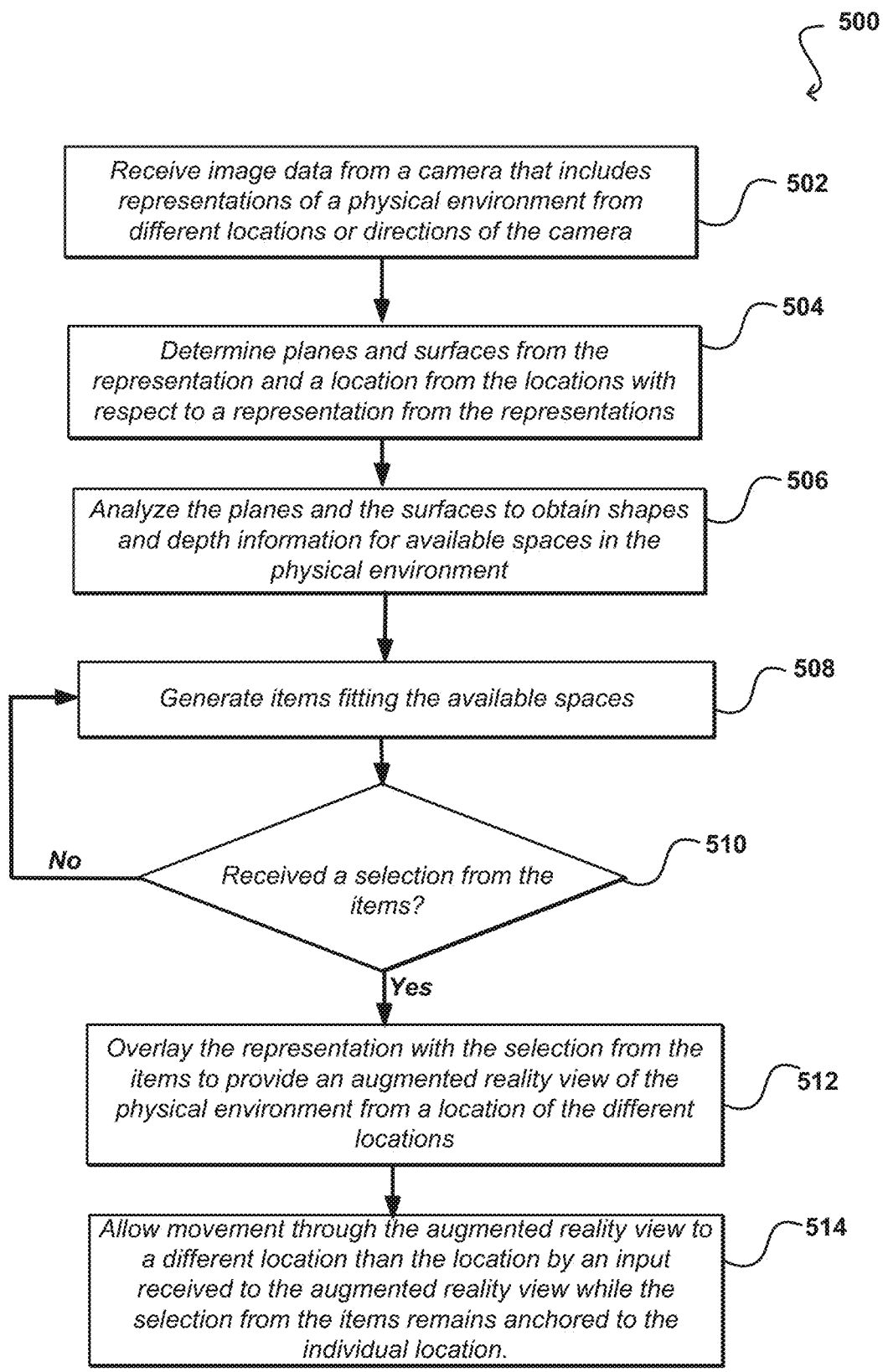
FIG. 5A is a flow diagram of an example process for curating environments from representations of a physical environment that may be used to sample items for procurement via an augmented reality interface in accordance with various embodiments.

FIG. 5A is a flow diagram 500 of an example process for curating environments from representations of a physical environment that may be used to sample items for procurement via an augmented reality interface in accordance with various embodiments. Sub-process 502 receives image data from a camera. The image data may be, alternatively, received from other sources, such as previously stored data in a memory area associated with the camera and from third-party photos. In an aspect, the image data includes a live camera view of the physical environment. In yet another aspect, the image data includes two or more representations of the physical environment from different locations of the camera or from different directions of the camera.

Sub-process 504 determines planes and surface from the representations. This in essence may provide the 3D model of the planes and surfaces as related to each other and the viewpoints from which the representations were captured. The representations are considered associated by the location and time of capture of the representations. A further method is described herein for using session identifiers to associate representation. The session identifiers may be associated with specific users via user identifiers (IDs). The sessions may be shared publically or privately by the associated user. In an example, this may be by adding privacy tags to the session identifiers. In another example, points of interests between representations may be used, along with or independent of, the location and time information of capture of the representations, to associate the representations. The planes and surfaces may be determined by allowing the system executing process 500 to use a neural network to recognize shadows between planes and surfaces, and to mark edges in the representations. In an example, the planes and surfaces may be determined after edges are marked in the representations by user interaction with the representations. The planes and surfaces are analyzed using such tools as an AR scale and/or a neural network. For example, the AR scale may be used to find the relative position of the camera to the planes and the surfaces, and/or to find the relative position within each of the planes and the surfaces in various permutations and combinations of the planes and the surfaces. The neural network aspect allows the system to recognize points of interests in the planes or the surfaces, and allows the system to correlate measurements across the points of interests from prior training data. In an example, points of interest may be determined by corners in the planes and the surfaces, and a measure of the distance between corners being fixed or within a threshold, from prior data, causing information from the prior data (i.e., including prior depth and shape information) to be applied presently to describe depth information and shapes of available spaces marked within the physical environment. Such available spaces may be the spaces 324A, 324B illustrated in FIG. 3A.

Step 506 provides a curated environment with the planes, the surfaces, and the available spaces known to the system and available in an AR view to the user. In an example, the planes and the surfaces are measured using an AR scale to find relative measurements between the planes and from the planes to the surfaces. This information defines the available spaces when there are no items in the relative measurements between the planes and to the surfaces. In an example, there may be items within the relative measurements, but identification of these items and an area and volume estimate may be applied to reduce the available spaces in the relative measurements. Alternatively, replacement items may be suggested for the items existing within the available spaces.

Sub-process 508 generates items that fit the available spaces. As explained elsewhere in this disclosure, such a process relies in part on the shapes and depth information obtained from the analysis of the representations in the curated environment using AR scales and neural networks. In the neural networks example, one neural network or multiple neural networks (designed to the same goal as a single neural network and is interchangeably referred to herein as a neural network) is trained to recognize items or spaces within the planes and the surfaces of the representations. Size information is obtained for the items and may reduce the spaces available within the planes and the surfaces. In a further example, the shapes and depth information may be defined by user interfacing with the representations via an AR marker. For example, the relative location information for the planes and the surfaces, as obtained from the image data, enables an interactive input to mark areas in the representation as an available space. Once marked, the relative location information works with the AR scale to determine coordinates in the marked areas. The coordinates are 3D coordinates and are used to calculate area and volume of the available space. The available space may be generated to be visually apparent in the 3D model of an underlying representation of a physical environment. This is because the available space is determined using the planes and the surfaces. However, existing items in the physical environment may be included in the 3D model or may be separately interfaced with the 3D model. This may be the case as the 3D model without the existing item allows for overlaying a new item in the available space—masking the existing item. For the new items, items in a database that are known by their outer-most dimensions may be matched to the available space. The outer-most dimensions refer to placement of a bounding box to the outer-most corners of each available item in an inventory, and determining a fixed shape area and a fixed shape volume to match with the available space. This is done so as to account for items with variable shapes and sizes.

Items may be provided in a listing or in a floating area of an AR view over the curated environment that includes the planes, the surfaces, and the available spaces. Sub-process 510 determines if a selection from the items is received. When no selection is received, further items are generated for the available spaces. When a selection is received, then the selected item alone may be overlaid in one of the representations to provide an augmented reality view of the physical environment from a location of the different locations. The location represents the location at which a camera captured the representation, for instance. The selected item is anchored through its anchor point to the plane of the representation, as discussed throughout this disclosure, including with respect to FIGS. 4E-4G. Sub-process 514 allows movement through the augmented reality view to another location of the different locations by selection of anchor points in the AR view while the selected item remains anchored to the individual location. This process represents movement in the curated environment with the selected item fixed in position and viewable from different angles in the AR view.

Figure 5B:
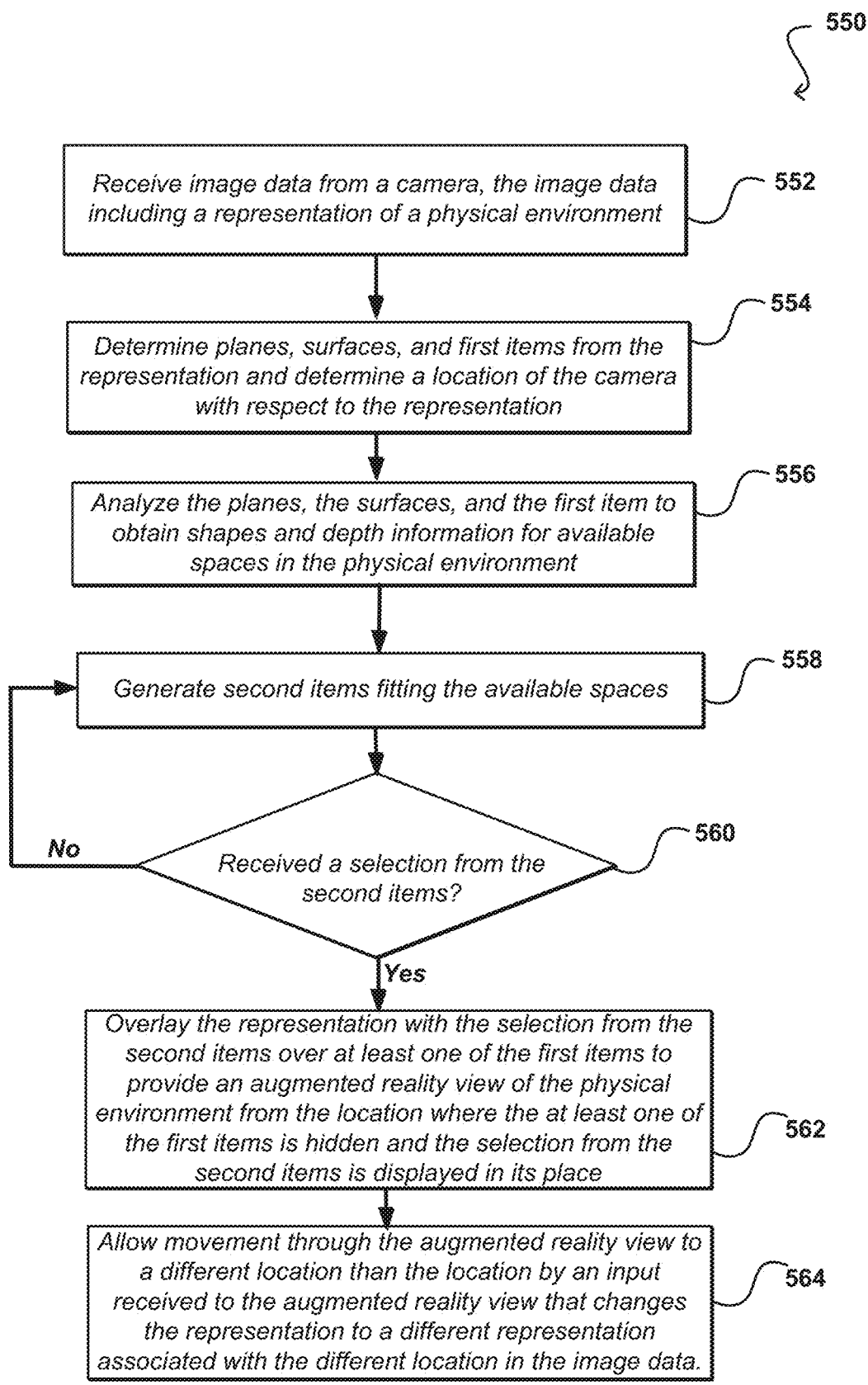
FIG. 5B is a flow diagram of an example process for curating environments from representations of a physical environment and replacing items in the physical environment with items for procurement via an augmented reality interface in accordance with various embodiments.

FIG. 5B is a flow diagram of an example process 550 for curating environments from representations of a physical environment and replacing items in the physical environment with items for procurement via an augmented reality interface in accordance with various embodiments. Sub-process 552 receives image data from a camera. The image data, as in the case of process 500, may be alternatively received from other sources, such as previously stored data in a memory area associated with the camera and from third-party photos. In an aspect, the image data includes a live camera view of the physical environment. In yet another aspect, the image data includes a representation of the physical environment from a location of the camera or from direction of the camera. The image data may include other representations of the physical environment from other locations or other directions of the camera capturing the physical environment.

Sub-process 554 determines planes, surfaces, and first items from the representation. In the manner of process 500, sub-process 556 analyzes the planes, the surfaces, and the first item to obtain shapes and depth information for available spaces in the physical environment. In an aspect, the shapes and the depth information includes item-related shapes and depth information associated with the first items. This may be distinct from shapes and depth information for empty spaces. In usage herein, empty spaces are devoid of items, while available spaces include empty spaces and spaces with items that may be replaced via and AR view overlay. The item-related shapes and depth information may be generated in a similar manner as the shapes and the depth information for empty spaces, as explained with respect to process 500. However, the use of outer-most points to calculate area and volume for an item may be used in generating the item-related shapes and depth information. Sub-process 558 generates second items to fit the available spaces—including the spaces containing first items. Sub-process 560 determines if a selection from the second items is received. When no selection is received, further second items are generated. When a selection is received, sub-process 562 is performed.

Sub-process 562 overlays the representation with the selection from the second items over at least one of the first items to provide an augmented reality view of the physical environment from the location. In the AR view, the at least one of the first items is hidden by a camouflage using similar coloring as a plane or a surface underlying the at least one of the first items. The selection from the second items is displayed in the place of the at least of the first items. Further, sub-process 564 allows movement through the AR view to a different location than the location. The movement may be by an input received in the AR view and represents a traversal of the curated environment with the selection from the second items anchored to the plane previously displaying the at least one of the first items. The movement to the different location changes the representation to a different representation associated with the different location in the image data, and provides a different view of the selection from the second items.

Figure 6:
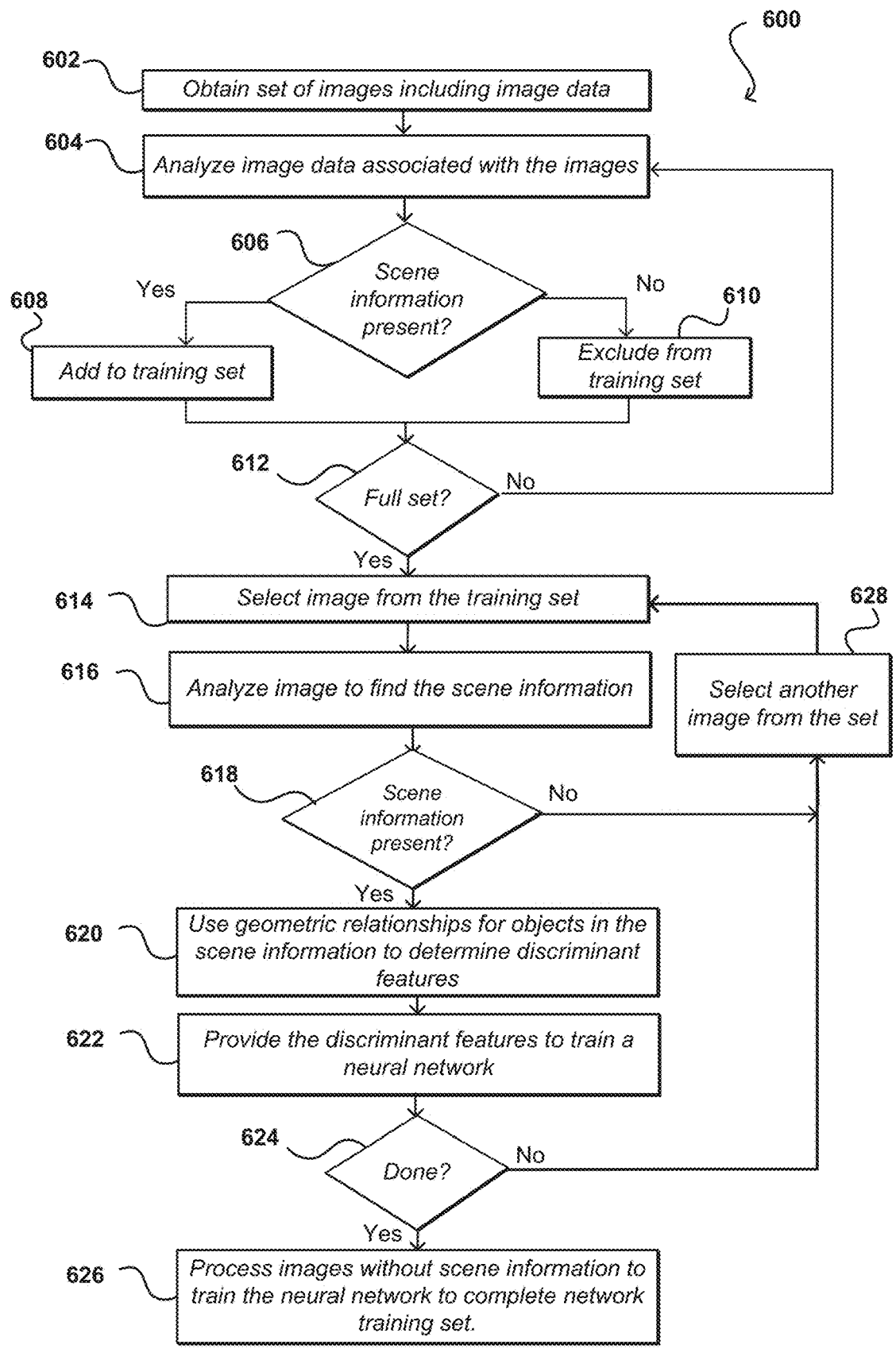
FIG. 6 illustrates an example training neural network process for training a neural network to recognize physical environments in accordance with various embodiments.

FIG. 6 illustrates an example NN training process 600 for training an NN or other machine learning-based approach to recognize physical environments using objects and other scene information from spatial information associated with image data of a live camera view or a representation of the physical environment for curating an environment underlying an AR view. The NN training process 600 includes multiple sub-processes 602-626 that work collectively to train the NN. Sub-process 602 obtains a set of images including image data. The set of images may be from an image database that stores images to improve the NN. As previously described, the term images used herein refers to representations of a physical environment, such as images, videos (including video frames), and live camera views on a display of a computing device. Accordingly, this NN training process 600 is applicable to recognize physical environments in each of the images, the videos (including the video frames), and the live camera views.

Sub-process 604 analyzes the image data associated with the images. Such analysis could provide a determination, via sub-process 604, that certain images are likely to include scene information. In an example, scene information includes recognizable coordinates or features for representations of objects in the images. In sub-process 604, for instance, each image may be analyzed for metadata, color variations (e.g., using histograms), object markers, etc. When there is a likelihood of scene information as detected by sub-process 606, the corresponding image is added to a training set, as in sub-process 608. Images considered to not include scene information may be excluded from the training set, as in sub-process 610. In an example, images that do not include scene information may be those images that do not include coherent coordinate points. Image filtering may be applicable to determine if boundary variations exist in a manner that indicates multiple objects or different features (scene information) exist in an image. Alternatively, color variations are a basis to filter images as including scene information than images with no significant color variations. Sub-process 612 determines when a full set of images are present in both, the training set and the set excluded from training images.

Sub-process 614 selects an image from the training set for training one or more NNs. Sub-process 616 analyzes the image to find the scene information using similar processes as in sub-process 604, for instance. When it is determined that scene information are present, via sub-process 618, then further processing as in sub-processes 620-622 commences. For example, metadata or other identifiers may be used to train an NN to classify images using their scene information. Alternatively, coordinates or features are applicable to train NNs. In sub-process 620, geometric relationships in coordinates for each scene information is used to determine discriminant features for the scene information. Such training enables a trained NN to determine room types based on the discriminant content of the image data. As previously described, particular features exist in a living room that are seen as discriminant other spaces, such as a kitchen or a bathroom. These features are typically objects—such as a bed, a couch, a stove, etc. With this information trained into a NN, the trained NN is able to discern from the image data the type of objects in an image, and therefore, is capable of determining the room type for the image.

NNs (NNs) typically use a gradient descent with a large amount of training data, but other training algorithms are applicable, including stochastic approaches and Levenberg-Marquardt training. In an aspect of the present disclosure, convolutional NNs are used in the training to determine room type using scene information. An NN may be trained to distinguish multiple data classifications or clusters (each corresponding to a different object representing scene information) or may be trained to distinguish a single data classification or cluster (corresponding to one object representing a scene information). When a single data classification is trained to an NN, multiple such single data classification NNs may be required, with each being capable of determining specific scene information—e.g., specific objects or geometric features. Convolutional NNs are a family of statistical learning models used in machine learning applications to estimate or approximate functions that depend on a large number of inputs. The various inputs are interconnected with the connections having numeric weights that can be tuned over time, enabling the networks to be capable of "learning" based on additional information. The adaptive numeric weights can be thought of as connection strengths between various inputs of the network, although the networks can include both adaptive and non-adaptive components. NNs exploit spatially-local correlation by enforcing a local connectivity pattern between nodes of adjacent layers of the network.

In some embodiments, individual nodes and/or layers of the NN may be implemented by one or more functions stored as computer executable instructions stored in a memory. For example, input layer nodes may include memory for storing input values. Each input layer node may be associated with a function stored as computer executable instructions in memory. The function may be applied to the input value and a resulting output value may be passed to one or more hidden layer nodes connected to the input layer nodes. Similarly, each hidden layer node may be associated with a function having N inputs (received from N connected input layer nodes). These functions may also be stored as computer executable instructions and/or data for computing values to be sent to one or more output layer nodes. The output layer nodes may be connected to the hidden layer nodes and may include memory for storing output values indicative of one or more attributes, entities, or concepts that the trained NN can identify, such as product attributes shown on web pages or catalogs.

In various embodiments, the nodes may form a directed graph or other data structure, with each layer of nodes occupying a different portion of the graph. Different layers of the network can be composed for different purposes, such as convolution and sub-sampling. In one example there is an input layer which along with a set of adjacent layers forms the convolution portion of the example network. The bottom layer of the convolution layer, along with the lower layer and output layer, make up the fully connected portion of the NN. From the input layer, a number of output values can be determined from the output layer, which can include several products determined to be related to an input option. The NN is trained on a training data set, which may include the geometric relationships or features for scene information that define a room type. The training provides the NN with learning ability for the best feature representation for the discriminatory data to distinguish room types based on scene information.

Sub-process 622 provides the discriminant features to train a NN. In an example, coordinates of features associated with representations of an object from one or more training images of the set are provided as the discriminant features in a first order input to the NN. The NN may be a multi-layered NN model with multiple hidden layers indicating deep learning. An initial layer takes first level features of one or more objects. The multiple hidden layers take the hidden state of an element as input, enriching it by multiplying it with the hidden states of other elements, e.g., other coordinates relating to other objects than the input objects. The number of hidden layers is chosen based partly on the number of input variables, the weights assigned to each node in the hidden layers, any included bias values for each node, and the number of epochs of training to secure the least error in the trained NN. An output from the training NN is back propagated into the network to determine if the input values are similar to the back propagated output. An error in the value difference is used to vary the weights and the biases during a forward propagation of the same training NN. Once the error is found to be the least possible in multiple epochs of the training, then the training is stopped, via sub-process 624, and the training NN is considered a trained NN. When multiple images are available, the sub-processes 614-624 are repeated, via sub-process 628, to provide sufficient discriminant features to train the NN. Once sufficient discriminant features are available, the above training proceeds to reduce the NN error to the least and to attain a trained NN.

The data values associated with the trained NN are considered trained data values, which are then applied to new images (e.g., image data of test images or live camera view) to determine if any of the features of the new images classify within the trained data values. When minimum error is returned for new image data, then one or more classifications are considered to have occurred for the new images, which in turn indicate that features of representations of objects in the new images are recognizable as similar to ones in the trained data values. In a further example, the trained NN may be further processed using image data from images without scene information, as in sub-process 626, to improve the trained NN. Once a new image is determined as including certain types of scene information, the collective information from the scene information describe the room type—e.g., as previously explained, a trained NN determines scene information, such as couches and tables, from the new image, which in turn describes that a room type in the new image is a living room.

In another implementation, one or more portions of image data corresponding to images from the training set of images may be applied to train one or more NNs. In such an implementation, position information is obtained using one or more bounding boxes in the images for respective selected portions. The bounding boxes represent areas of interest in the images for training NNs. The bounding boxes may be pre-determined or identified upon request of a user (e.g., administrator) of the system. In an example, the bounding boxes are implemented to retrain aspects of a trained NN. Once the position information is obtained, a new NN may be trained or an existing NN may be retrained using similar processing as described with respect to FIG. 6. Pertinently, as input to train NNs in FIG. 6, only selected portions of images (including zoomed-in portions) are analyzed in the filtering and classification processes to build the NNs to discriminate scene information for room types and color information for color in the portions of the images. Once completed, the new or retrained NNs are tested using portions of other images or the same image that was used to train (or retrain) the NN. The trained (or retrained) NNs for the portions of the image data are provided for similarity analysis for color and scene information, and to provide color, texture, room type, and other information deemed pertinent to generating types of items and subsequently the associated items.

NNs are example machine learning process for the present embodiments. However, other machine learning processes such as support vector machines (SVM), Gaussian processes, random forests, and classification and regression trees are applicable to train NNs, from prior image data, to determine color and scene information, and to provide color, texture, room type, and other information deemed pertinent for new images.

Figure 7:
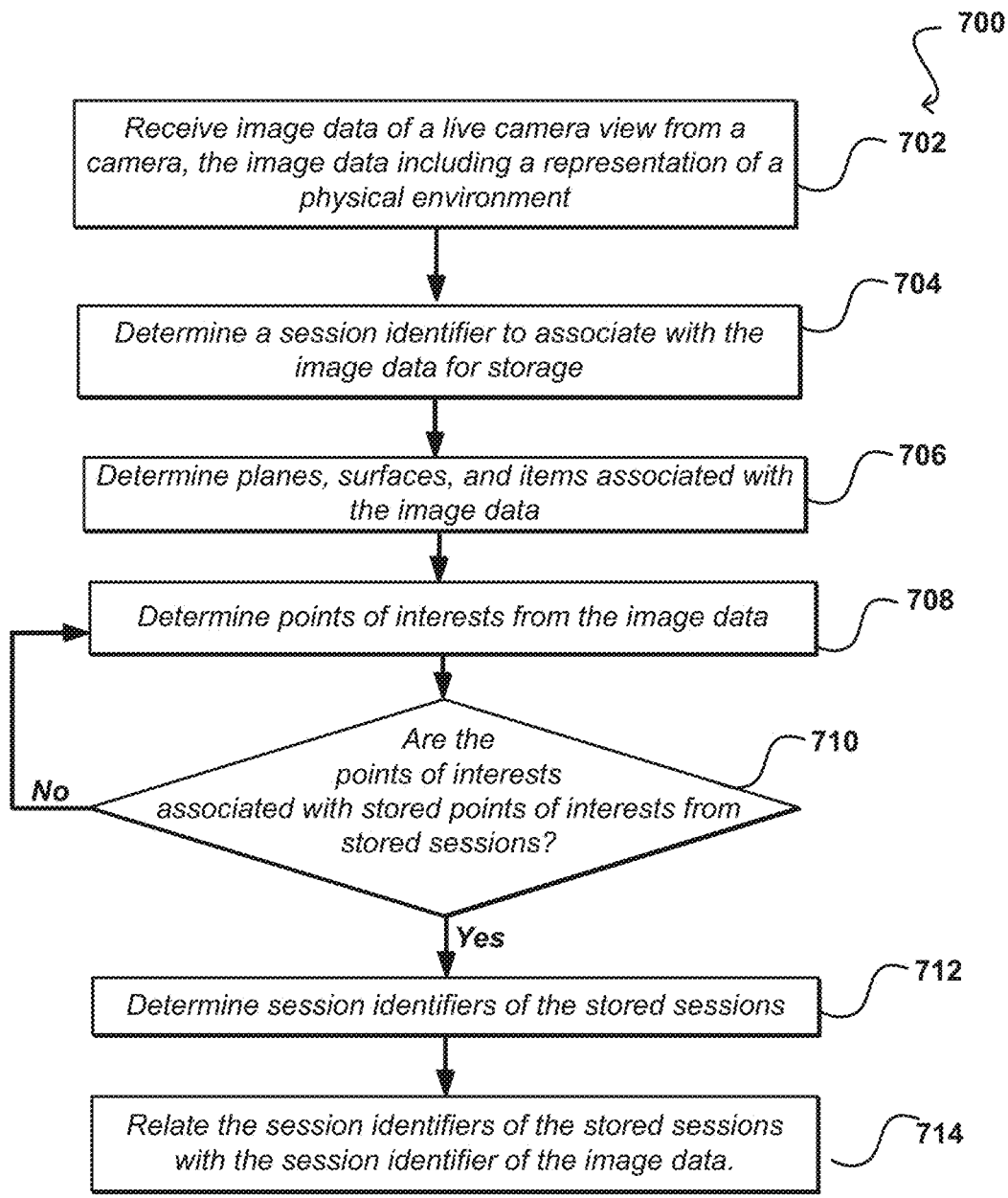
FIG. 7 is a flow diagram of an example process for curating environments from representations of a physical environment by adding to a curated environment using session identifiers in accordance with various embodiments.

FIG. 7 is a flow diagram of an example process 700 for curating environments from representations of a physical environment by adding to a curated environment using session identifiers in accordance with various embodiments. Sub-process 702 received image data of a live camera view from a camera during a session of image capturing. The image data includes a representation of a physical environment. Sub-process 704 determines a session identifier to be associated with the representation in the image data for storage of the representation. In an example, the session identifier may be encrypted and may include coded nomenclature. In an alternate aspect, the session identifier includes location, direction, and time information for when the representation of the physical environment was captured. This information may be, in an alternative implementation, stored as a metadata, within the session. The session identifier may be generated randomly (if under the encrypted process) or may be generated based on uniqueness of the time of capture. As in the case of the processes 500, 550, the present process includes a sub-process 706 for determining planes, surfaces, and items associated with the image data—i.e., within the representation.

Sub-process 708 determines points of interests from the image data. The points of interests may be to the representation as a whole including the planes, the surfaces, and the items. A determination is made, via sub-process 710, whether the points of interests are associated with stored points of interests from stored sessions. In an example, the points of interests may also include location information of the camera or source of the image data, relative location information of the camera or the source to the planes, the surfaces, and the items; and also relative location information of the planes to the surfaces, and to the items. In an example, the relative location information may be unique for a room that includes certain items. Then identifying this uniqueness from the points of interests of the representation to stored points of interests would indicate that stored representations in the stored sessions are related to the representation recently captured. Sub-process 712 determines the session identifiers for the stored session. Sub-process 714 then relates the session identifiers of the stored sessions with the session identifier of the image data. In this manner, the curated environment may be augmented or continuously built from image data received for a physical environment at different times and from different locations, and also from different sessions.

The process 700 of FIG. 7 also enables association of an image captured from a live camera view or at a later point with 3D planes and surfaces within the image. In an example using the process 700, image data in sub-process 702 may correspond to a single image. A session identifier is determined for the image. Then planes, surfaces, and items associated with the image data may be determined from the image. Points of interests may be determined from one or more of the planes, surfaces, and items, and may also take into consideration location and time of capture of the image data. A determination is made for matching points of interests from stored sessions to points of interests. When the matching points of interests exist, the present system allows association the planes, the surfaces, and the items from the stored sessions to the image, and further allows a user to traverse an AR view that includes the image and other images to adding or remove items in the image (and images from the stored sessions). Such a process allows creation of 3D models of the planes, the surfaces, and/or the items, and then allows mapping or associating of the 3D models—e.g., at least the planes and surfaces—to the image. Such mapping or associating is also to subsequent images captured from the same location at any point in time. As such, the present system and processes enables separation of image data and planes and surfaces in the image data—now represented by the 3D models. The present system and processes also allow rejoining of the image data and the planes and surfaces by an AR view overlay of the 3D model to the image data. The 3D models may be virtual planes and virtual surfaces in solid (or other patterns), provided overlaying the image (and images from the stored sessions). Alternatively, the 3D models may be wire models (e.g., displaying boundaries of the planes and surfaces (and optionally, of items existing or previously added in the 3D model).

Figure 8A:
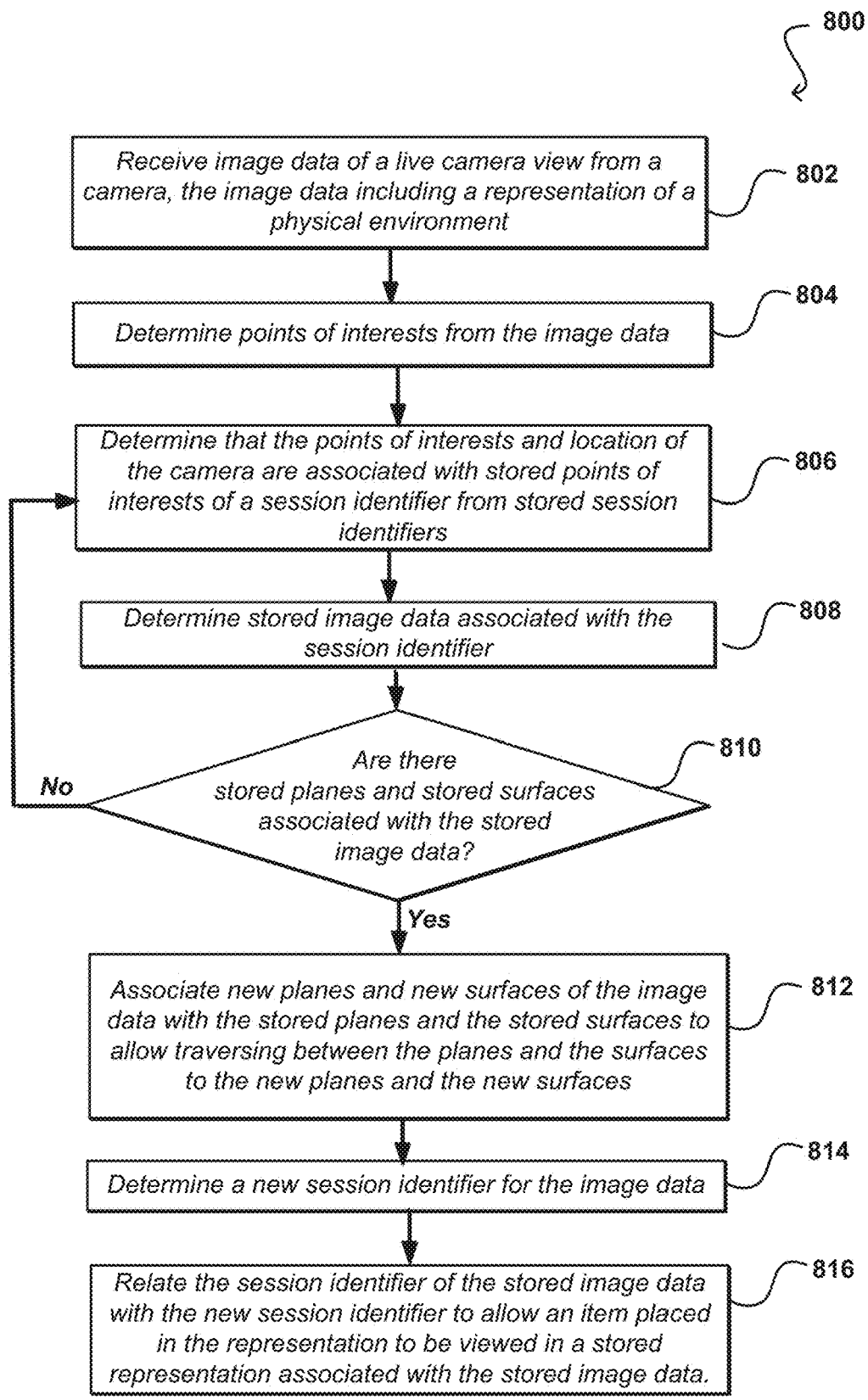
FIG. 8A is another flow diagram of an example process for curating environments from representations of a physical environment using points of interest and session identifiers in accordance with various embodiments.

FIG. 8A is another flow diagram of an example process 800 for curating environments from representations of a physical environment using points of interest and session identifiers in accordance with various embodiments. The example process 800 works independently or together with example process 700. Sub-process 802 receives image data of a live camera view from a camera. The image data includes a representation of a physical environment. Sub-process 804 determines points of interests from the image data in a similar manner as described with respect to the process of FIG. 7. Sub-process 806 determines that the points of interests and location of the camera from sub-process 802 are associated with stored points of interest of a session identifier from stored session identifiers. This may be by continuous comparison of ratios generated from the points of interests with stored ratios in a database or by one or more trained neural networks that can distinguish multiple ratios for planes, surfaces, and for items.

Sub-process 808 determines stored image data associated with the session identifier. Sub-process 808 determines if there are stored planes and stored surfaces associated with the stored image data. When there is no such information, further session identifiers identified as relevant may be used. In such an implementation, the determination of relevant session identifiers may be by the neural network finding a score by comparing stored points of interests for each stored session and the points of interests for the image data of sub-process 804. A threshold score may be used to find the relevant session identifiers. Then each of the relevant session identifiers may be checked for stored planes and stored surfaces via sub-process 810. Sub-process 812 then associates new planes and new surfaces of the image data from sub-process 804 with the stored planes and the stored surfaces of the most relevant session. The association may be by stitching together or associating as anchor points, the stored planes to the new planes and stored surfaces to the new surfaces. This allows creation of a curated environment and allows users to traverse from the representation captured in sub-process 802 to a prior representation stored for the physical environment. A new session identifier is determined, via sub-process 814, for the image data of sub-process 804. Sub-process 816 relates the session identifier of the stored image data with the new session identifier. This allows items placed in the representation captured in sub-process 802 to be viewed from the prior representation of the stored image data. Such an implementation allows an item to be viewed in a representation across times (day time, noon time, night time, etc.), across seasons (in external physical environments), and across changes previously made to the physical environment by combining with the process 550, for instance. As such, a person of ordinary skill reading the present disclosure will be able to mix the various processes and systems to use them interchangeably, without departing from the scope of the disclosure.

Figure 8B:
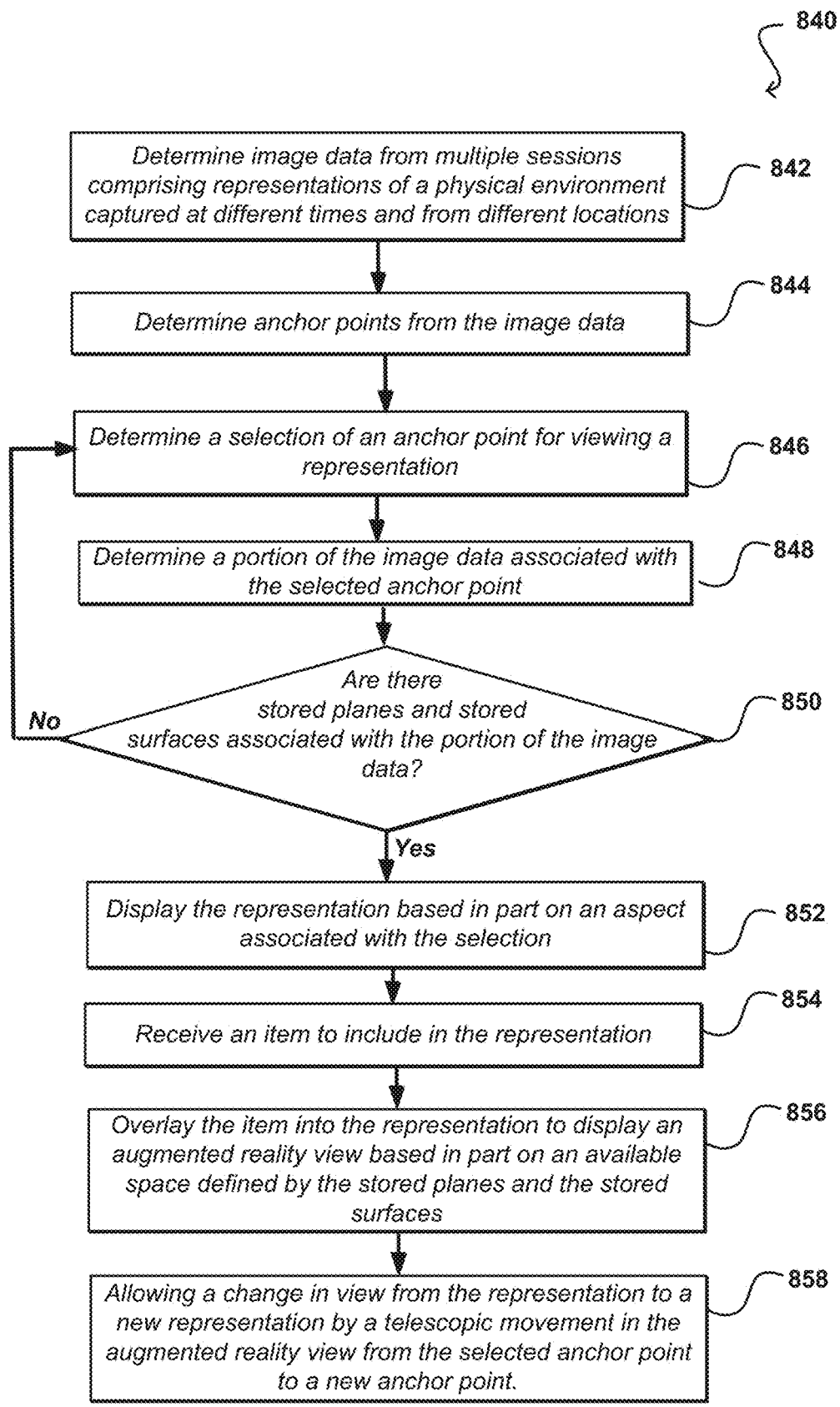
FIG. 8B is yet another flow diagram of an example process for allowing traversal of a curated environment using anchor points representing camera location for representations of a physical environment at time of capture of associated representations in accordance with various embodiments.

FIG. 8B is yet another flow diagram of an example process 840 for allowing traversal of a curated environment using anchor points representing camera location for representations of a physical environment at time of capture of associated representations in accordance with various embodiments. Sub-process 842 determines image data from multiple sessions either previously stored and accessible to the sub-process, shared with the sub-process, or captured in burst times using a camera that is continuously moving or continuously changing directions. Sub-process 844 determines anchor points from the image data. The anchor points, as used in this process, refer to locations and/or directions at which the representations are captured. Sub-process 846 determines a selection of an anchor point for viewing a representation of the representation. In an example, this may be a selection to start a display of a curated environment or may be a selection after the display of the curated environment has begun. When the selection starts the display of the curated environment, then the anchor points may be default anchor points for which representations must exist. When the selection is after the curated environment is already displayed, then the anchor points may include other locations and/or directions than the default directions and/or locations at which representations were captured and stored.

Sub-process 848 determines that a portion of the image data is associated with the selected anchor point. Sub-process 850 determines if there are stored planes and stored surfaces associated with the portion of the image data. When no such information is found, another anchor point may be selected. When such information is found, the representation associated with an aspect of the selection is displayed.

In an example, the anchor points displayed may be based on seasons, times, location, or direction of capture of the associated representations. In such a circumstance, the anchor point may be displayed based in part on a filtering of all available anchor points for a particular physical environment at particular seasons, particular times, particular location, or from particular directions of capture. In such an example, the selection of an aspect of the anchor point results in the display of the representation associated with the selection. Sub-process 854 receives an item to include in the representation. Sub-process 856 overlays the items into the representation to display an augmented reality view based in part on an available space defined by the stored planes and the stored surfaces for the representation. Sub-process 858 allows a change in view from the representation to a new representation by a telescopic or other movement in the AR view from the selected anchor point to a new anchor point. Process 840 allows a user to add an item to a representation of a physical environment in a particular season or time of today. This implementation is useful for external physical environments and allows a user to switch the time of day or season while keeping the item in the AR view.

Figure 8C:
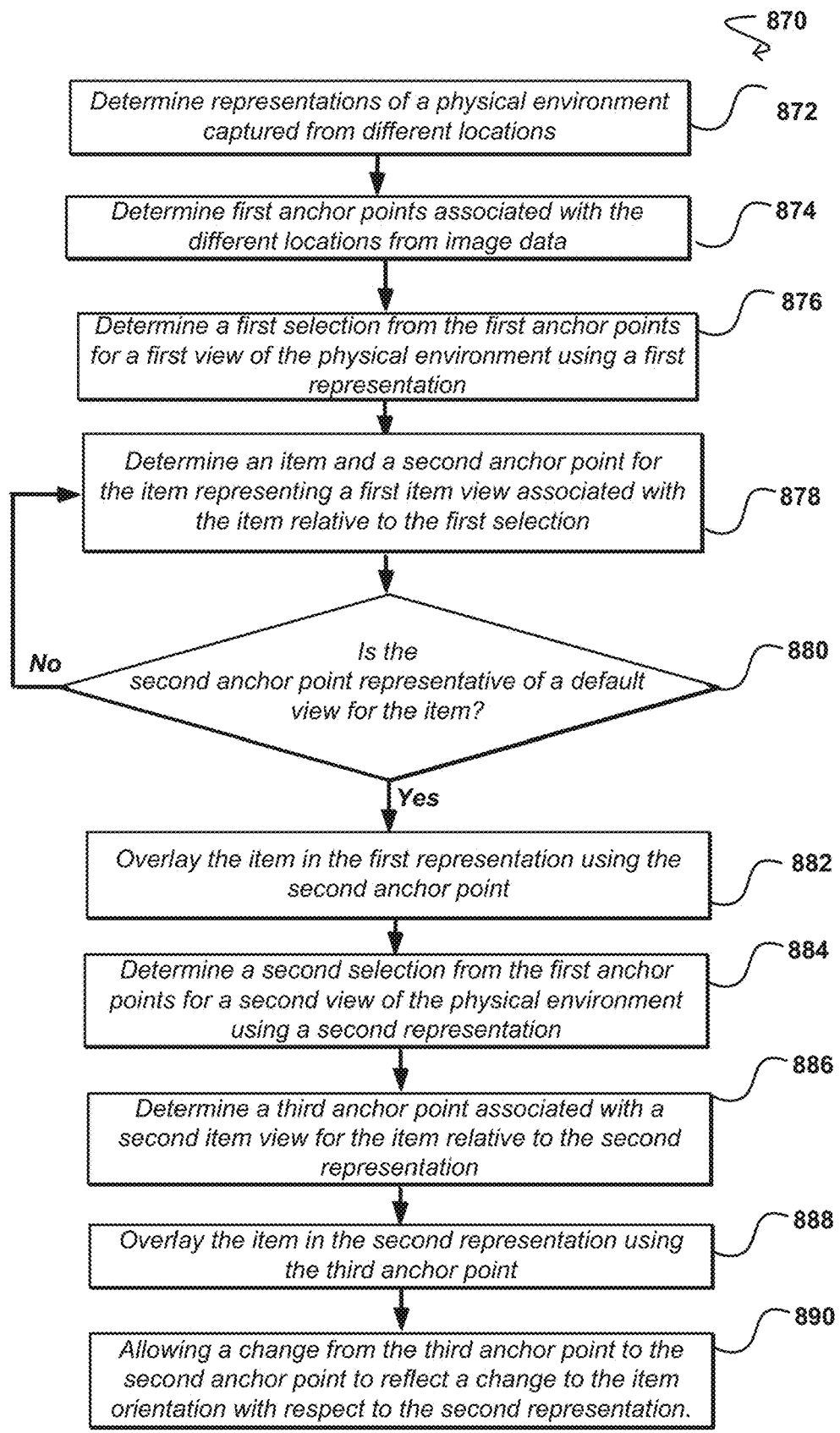
FIG. 8C is a further flow diagram of an example process for allowing changes to an item orientation in a curated environment using anchor points for the items in accordance with various embodiments.

FIG. 8C is a further flow diagram of an example process 870 for allowing changes to an item orientation in a curated environment using anchor points for the items in accordance with various embodiments. Process 870 allows changing orientations of an added item in a representation and allows a new orientation of the item to carry over to a new view of the representation from another location in the curated environment. Sub-process 872 determines representations of a physical environment captured from different locations. Sub-process 874 determines first anchor points that are associated with the different locations from the image data. In an example, the locations may be replaced or may be concurrently included with directions of the camera at the different locations. Sub-process 876 determines a first selection from the first anchor points for a first view of the physical environment using a first representation of the representations from sub-process 872. Sub-process 878 determines an item and a second anchor point. The second anchor points is associated with the item and represents a first item view associated with the item relative to the first selection from the first anchor points in sub-process 876.

Sub-process 880 determines if the second anchor point is representative of a default view for the item. When this is not the case, another anchor point may be selected for the item. When the second anchor point is representative of a default view for the item, then the item is overlaid in the first representation to create an AR view of the physical environment using the second anchor point. As such the view represented on insertion of an item in the representation is a default view for the item. In an example, the default view may be with respect to the first selection from the first anchor points for the first view of the physical environment. As such, a pre-determined relationship may be established between laying out items in a representation by aligning an anchor point of the item with an anchor point of the plane or surface. In this manner, when the anchor point for a plane or a surface is selected, the item is displayed automatically anchored in a default orientation. This may be understood using the example of FIGS. 4E-4G. In an example, marker 492A indicates that the opposite side of the table 482A is an anchor point. For a view of the representation in FIG. 4E, the table 482A is tagged to default its anchor point against the plane behind the couch. As such, the anchor point 488E, shown in the representation in FIG. 4G (60 degree view to the plane behind the couch), is the anchor point for the representation in FIG. 4E (90 degree view to the plane behind the couch). With this information, anchor point 488E is associated with the anchor point opposite marker 492A. So item 482A will always default to the view illustrated in FIGS. 4E, 4G. Thereafter, a user may rotate the item 482A as in FIG. 4F and anchor it to the plane behind the couch. In an example, popularity of an orientation of an item is measured and stored, and may be used to default the item in the most popular orientation than a manufacturer desired orientation—for instance.

Sub-process 884 demonstrates the above example, by determining a second selection from the first anchor points (associated with changing a view from the representation to a second representation). Sub-process 886 determines a third anchor point associated with a second item view of the item relative to the second representation. This is illustrated in the example of FIG. 4E. Sub-process 888 overlays the item in the second representation using the third anchor point as illustrated in the configuration 495B of FIG. 4G (compare this against the configuration in FIG. 4E including the orientation of the table and the viewpoint in the representation). Sub-process 890 allows a change from the third anchor point back to the second anchor point, which changes the item orientation with respect to the second orientation. This is reflected in configuration 495A of FIG. 4G.

In another implementation, generated items associated with aspects and item types may be stored with tags as to the orientation, location, direction, and other related information. Further, the item types improve the system classification or categorization of the items and improve response times with respect to providing items for default settings. For example, when a user provides an image of a car interior and when items are generated or provided for the car interior, the user or the system may assign and tag the items by appropriate tags. In subsequent use of the present system and process, when the same user or an unrelated user intends to request for items for a car interior, the user may first peruse previously stored items before taking another image of the car's interior. Alternatively, in response to an unrelated user's image of its interior, the present system and processes promotes stored items corresponding to car interiors to the unrelated user after recognizing the user's image as a car interior.

In yet another aspect, the system and processes described with respect to FIGS. 1-11 are also applicable in a virtual environment, such as a gaming environment. For example, when a user wishes to add items in a frame of a game and to use relevant items virtually, the user may present the frame of the game as an image. Edges are marked to define planes and surfaces in the image. Aspects and types of items are determined by an NN or selected, and items are obtained based in part on this information and for insertion into the video game frame. The items represent colors or items suited for the scene described in the video game frame. Alternatively, a user may be recommended virtual products, including device wall papers, photo editing applications, devices, images, and other procurable items in response to a search based on colors in a video game frame. This process is also applicable to videos (e.g., movies, home movies, etc.)

Figure 9:
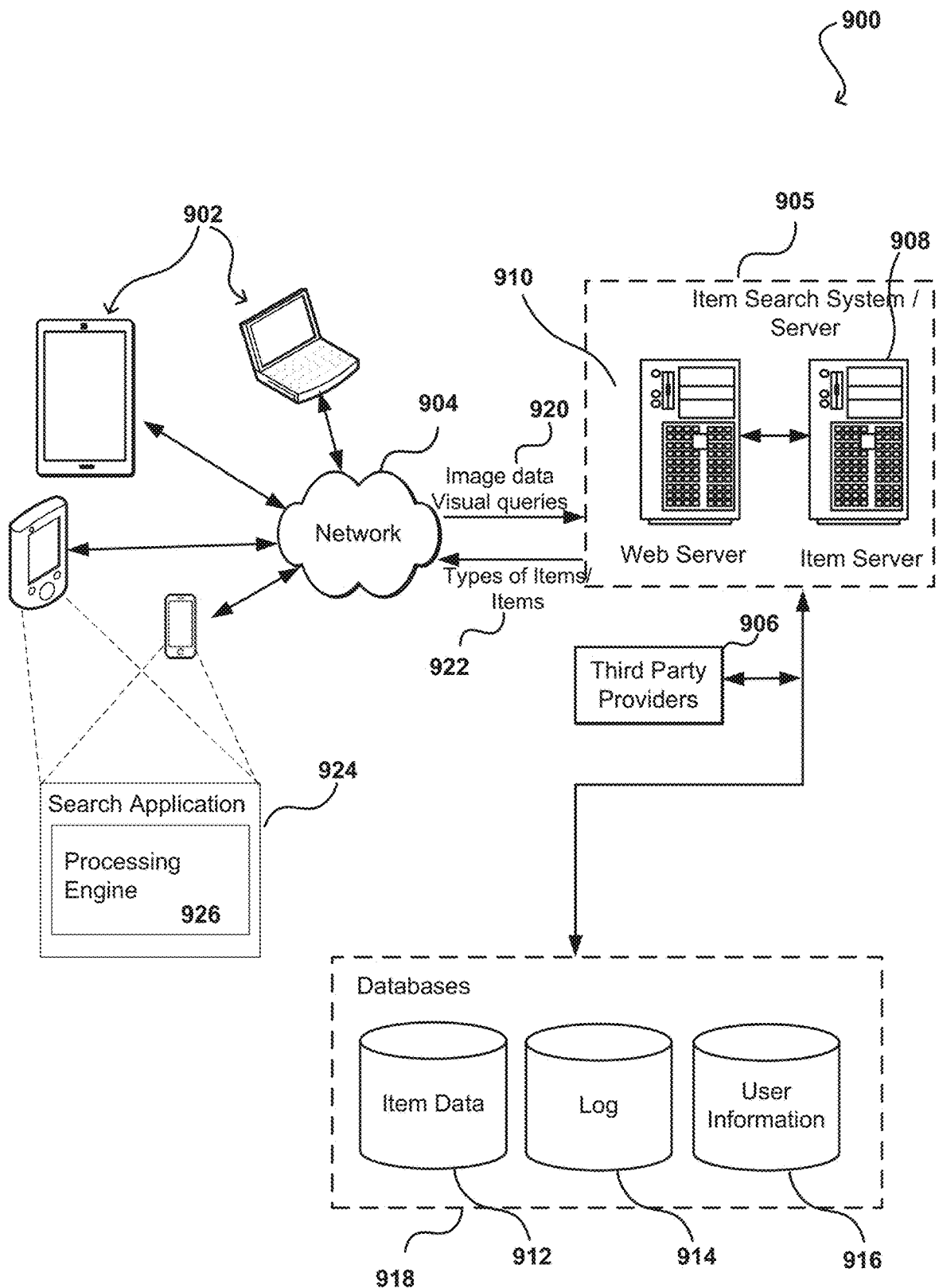
FIG. 9 illustrates an example architecture of a system for comparative information visualization in an augmented reality interface in accordance with various embodiments.

FIG. 9 illustrates an example architecture of a system 900 for comparative information visualization in an augmented reality interface in accordance with various embodiments. As will be appreciated, although a web-based environment is used for purposes of explanation, different environments may be used, as appropriate, to implement various embodiments. The system 900 includes computing devices 902, which can include any appropriate device operable capture images and/or to communicate images and product information over an appropriate network 904. Examples of such computing devices 902 include those described with respect to FIGS. 1B, 2, 3, 4B, 4D, 9 and 10, and can further include personal computers, tablets, ultrabooks, smartphones, cell phones, wearable watches and related devices, handheld messaging devices, laptop computers, set-top boxes, personal data assistants, electronic book readers and the like. Further, the computing device 902 may include a search application 924 for capturing images or the live camera view, for providing the interface of the types of items and the items themselves corresponding to the image data and the aspect determined for the captured images or the live camera view, and for communicating with the user and the product search system/server 905. The search application may include a processing engine 926 for performing one or more image processing functions, such as to train an NN (or NNs directed to a singular goal) to recognize scene and color information from the image data discussed with respect to FIG. 2. Further, third party providers 906 may provide item and categorizing information directly to the item search system/server 905. The third party providers may be distributors, manufacturers, resellers, or other entities associated with the item.

The network 904 can include any appropriate network, including an intranet, the Internet, a cellular network, a local area network or any other such network or combination thereof. The network could be a "push" network, a "pull" network, or a combination thereof. In a "push" network, one or more of the servers push out data to the client device. In a "pull" network, one or more of the servers send data to the client device upon request for the data by the client device. Components used for such a system can depend at least in part upon the type of network and/or environment selected. Protocols and components for communicating via such a network are well known and will not be discussed herein in detail. Communication over the network 904 can be enabled via wired or wireless connections and combinations thereof. In this example, the network includes the Internet, as the environment includes a web server 910 for receiving requests and serving content in response thereto, although for other networks, an alternative device serving a similar purpose could be used, as would be apparent to one of ordinary skill in the art.

The illustrative system 900 includes at least one application (or item/product) server 908 and a data store or databases 910. It should be understood that there can be several application servers, layers or other elements, processes or components, which may be chained or otherwise configured, which can interact to perform tasks such as obtaining data from an appropriate data store. Further, the web server 910 and the application (or product) server 908 are part of a product search system/sever 905, similar to description with regards to FIGS. 2 and 3A. As used herein, data store or database refers to any device or combination of devices capable of storing, accessing and retrieving data, which may include any combination and number of data servers, databases, data storage devices and data storage media, in any standard, distributed or clustered environment. The application server 908 can include any appropriate hardware and software for integrating with the data store 918 as needed to execute aspects of one or more applications for the client device and handling the image data and/or visual queries 920 for an application of the computing device 902. In response types of items, item listing, items, or products 922 are provided from the item or product search system/server 905. The application server 908 provides access control services in cooperation with the data store and is able to generate content such as text, graphics, audio and/or video to be transferred to the user, which may be served to the user by the Web server 910 in the form of hypertext markup language (HTML), extensible markup language (XML), or another appropriate structured language in this example. The handling of all requests and responses, as well as the delivery of content between the client device 902 and the application server 908, can be handled by the web server 910. It should be understood that the web and application servers are not required and are merely example components, as structured code discussed herein can be executed on any appropriate device or host machine as discussed elsewhere herein.

The data store 918 can include several separate data tables, databases or other data storage mechanisms and media for storing data relating to a particular aspect. For example, the data store 918, as illustrated, includes mechanisms for storing content (e.g., product data) 912 and user information 916, which can be used to serve content for the production side. The data store is also shown to include a mechanism for storing log or session data 914. It should be understood that there can be many other aspects that may need to be stored in the data store, such as page image information and access rights information, which can be stored in any of the above listed mechanisms as appropriate or in additional mechanisms in the data store 918. The data store 918 is operable, through logic associated therewith, to receive instructions from the application server 908 and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a web page that the user is able to view via a browser on the computing device 902. Information for a particular product can be viewed in a dedicated page or window of the browser after overlaying in the image, for instance. In such an implementation the overlay include hyperlink, clickable, or selectable aspects to allow the product information to open in a same application as the image or a separate application, such as a browser, of the computing device 902.

Each server 908, 910 typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are readily known to a person of ordinary skill after reading the present disclosure, and may be suited from commercially available components by persons having the ordinary skill in the art, particularly in light of the disclosure herein.

In some embodiments, the web server 910, product server 908, and similar components, can be considered to be part of a product search system 905 and, broadly, of a control plane 905. The handling of all requests and responses, as well as the delivery of content between the computing devices 902 and the product server 908, can be handled by the web server 910. The web server 910 and item/product server 908 are merely example components. However, more or fewer components can be used as structured code can be executed on any appropriate device or host machine as discussed elsewhere herein.

The data plane 918 includes one or more resources, servers, hosts, instances, routers, switches, databases, other similar components, or a combination thereof. The resources of the data plane 918 are not limited to storing and providing access to data. Indeed, there may be several product servers, layers, or other elements, processes, or components, which may be chained or otherwise configured, and which can interact to perform tasks including, for example, obtaining data from an appropriate database. As used in this specification, database also refers to any device or combination of devices capable of storing, accessing, and retrieving data, which may include any combination and number of data servers, databases, data storage devices, and data storage media, in any standard, distributed, or clustered environment.

The databases of the data plane 918 can include several separate data tables, databases, or other data storage mechanisms and media for storing data relating to a particular aspect. For example, the data plane 918 illustrated includes mechanisms for storing product data 912 and user information 916, which can be used to serve content. The data plane 918 is also shown to include a mechanism for storing log data 914, which can be used for purposes such as reporting and analysis. The data plane 910 is operable, through logic associated therewith, to receive instructions from the product server 908 and to obtain, update, or otherwise process data, instructions, or other such information in response thereto, as described above.

Each server typically includes an operating system that provides executable program instructions for the general administration and operation of that server, and typically will include a computer-readable medium storing instructions that, when executed by a processor of the server, enable the server to perform its intended functions. Suitable implementations for the operating system and general functionality of the servers are known or commercially available, and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 9. Thus, the depiction of the system 900 in FIG. 9 should be taken as being illustrative in nature and not limiting to the scope of the disclosure.

Figure 10:
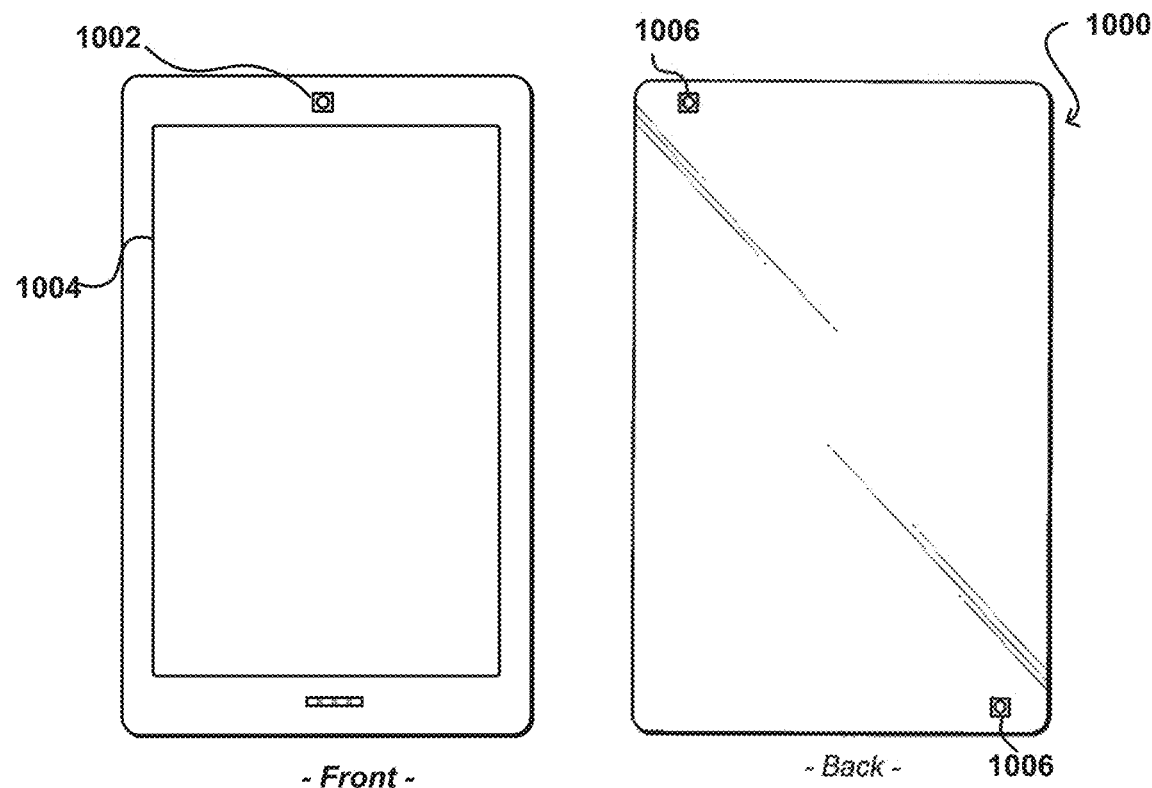
FIG. 10 illustrates an example computing device for performing one or more of the disclosed embodiments in accordance with various embodiments.

FIG. 10 illustrates an example of a computing device 1000 (in the front and back views) that is available for use in accordance with various embodiments. Such a computing device 1000 is similar to those described with respect to FIGS. 1B, 2, 3, 4B, 4D, 9 and 10. Screen 1004 is provided to display the various UIs in the various embodiments above. Computing device 1000 includes a front facing camera 1002 for interfacing with the UIs, but also, and preferably, includes one or more back facing cameras (e.g., reference numerals 1006) that interfaces with the UI for performing the various embodiments herein.

Figure 11:
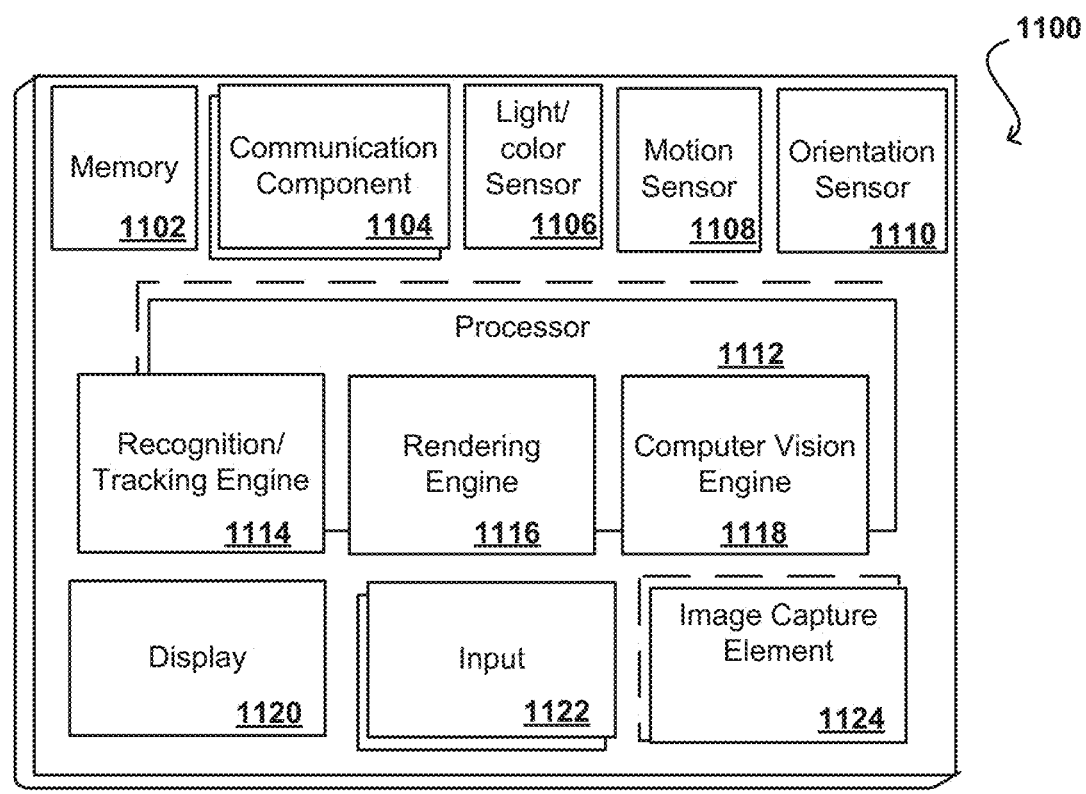
FIG. 11 illustrates example components of the computing device of FIG. 10 in accordance with various embodiments.

FIG. 11 illustrates an example configuration of components 1102-1124 of an example computing device 1100, such as computing device 1000 illustrated in FIG. 10, or the client or computing devices generally disclosed throughout this disclosure. Components 1102-1124 are a set of basic components for a computing device, but alternative or different arrangements are applicable for any of the disclosed computing devices in this disclosure, without changing the features in the embodiments above. In the example of FIG. 11, the computing device 1100 includes at least one processor 1112 for executing instructions that can be stored in a memory device or element 1102. As would be apparent to one of ordinary skill in the art, upon reading this disclosure, that the computing device 1100 can include many types of memory, data storage or computer-readable media, such as a data storage for program instructions for execution by the processor 1112. The same or separate storage can be used for images or data, and a removable memory can be available for sharing information with other devices. Further, any number of communication approaches can be available for sharing the information with other devices. Furthermore, it would also be apparent to one of ordinary skill, upon reading this disclosure, that processor 1112 may be multiple processors, each with processing tasks for the embodiments here, and may collectively act as a processor for the embodiments herein.

The computing device 1100 includes at least one type of screen or display element 1120, such as a touch screen, electronic ink (e-ink), organic light emitting diode (OLED) or liquid crystal display (LCD), although devices such as portable media players might convey information via other means, such as through audio speakers. The computing device 1100, in an example, also includes at least two image capture elements (illustrated as a single block 1124, with underlying blocks for more image capture elements, marked in broken lines). In an example, at least one image capture element 1124 is positioned to determine a relative position of objects in its frame of view. For example, the image capture element 1124 is operable to image or capture image data from a user, people, or other viewable objects in the vicinity of the computing device 1100. As previously noted, the image capture element 1124 can include any appropriate technology, such as a CCD or CMOS image capture element having a sufficient resolution, focal range and viewable area, to capture an image of objects and ambient lighting as part of operating the computing device 1100. Methods for capturing images or video using an image capture element with a computing device are known in the art, upon reading this disclosure. Further, it is generally understood, from this disclosure, that image capture can be performed using a single image, multiple images, periodic imaging, continuous image capturing, image streaming, video, live camera view, etc. As discussed, IR imaging can also be used to locate and track features of a user.

A computing device, e.g., the computing device 1100, has at least two sensors or image capture elements (e.g., reference numerals 1124) with each capable of capturing image data with color information from the multiple sensors 1124. Additionally position information also provided via the sensors 1124, and is used to determine a three dimensional (3D) position of image or objects in a physical environment for the computing device 1100. Such a process uses a distance, as well as a relative projection direction, of light sources from the objects and the ambient environment for making such a determination of the relative position of the light source. Such an approach enables an accurate capture of color information.

Further, although the above-described light sources are along a plane for an object, it should be understood that the light paths can form a 2D array that is available from which to capture color for a semi-hemispherical range of angles and from which to direct the light reflected from objects to a 2D array of pixels (e.g., for a VGA chip) or other such configuration of the sensor 1106 or 1124. With an approach similar to that discussed throughout this disclosure, a computing device 1100 can determine the color information for each light exposed to the camera sensor, and can use that information to develop a histogram of colors for the image or live camera view. In at least an example embodiment, there are more than one sensor/light elements positioned about the computing device 1100 in order to capture color information from substantially any direction around the computing device 1100. When the light is received with sufficient angular range, the computing device 1100 can have two arrays on opposing sides and develop a reasonable lighting model to accurately describe the colors in the physical environment. The light from the physical environment is only recognized at substantially a thickness of the casing of the computing device 1000, and thus, is primarily the size of the sensor 1106, 1118 (and any electronic paths or connectors) is added to the interior of the computing device 1100.

The computing device 1100 additionally includes at least one orientation sensor 1110, such as an accelerometer, digital compass, electronic gyroscope or inertial sensor, which can assist in determining movement or other changes in orientation of the device. One of ordinary skill would recognize upon reading the present disclosure that the orientation sensor 1110 is, therefore, also capable of providing location information at the time of capture of image data via its digital compass. The device can include at least one additional input device 1122 that is available to receive conventional input from a user. This conventional input can include, for example, radio-communications type wand devices, hand or gesture sensors, a push button, touch pad, touch screen, wheel, joystick, keyboard, mouse, trackball, keypad or any other such device or element whereby a user can input a command to the device. The conventional input, in one example, interfaces with the UI to move pointers or indicators on the UI, as in the case of the finger or stylus discussed with reference to FIG. 4A. One more of the additional input device 1122, in an example, is connected to the computing device 1100 by a wireless IR or Bluetooth® or other link. In an embodiment, computing device 1100 might not include any buttons at all and might be controlled only through a combination of visual and audio commands such that a user can control the computing device without having to be in contact with the computing device.

Furthermore, the computing device 1100 includes, in another example, communication component 1104 representing various communication features for the computing device to commute with near and far devices. For example, using Bluetooth®, Wi-Fi®, and other communication protocols. A light/color sensor 1106 and a motion sensor 1108 are provided to enable the computing device to be used in various lighting environments and to enable the computing device UI to be controller by movement gestures as discussed with respect to FIG. 4A, for instance. A recognition and tracking engine 1114 is provided to track a user and vary the lighting effects from an added light source to the screen view when the computing device is moved. A rendering engine 1116 is provided to render image data as discussed with respect to above embodiments, when it is required to provide color or scene information from the computing device 1100.

In an example, the computing device 1100 uses the light/color sensor 1106 to determine whether the device is exposed to ambient light or is in relative or complete darkness. Such a light sensor 1106 is beneficial in a number of ways to provide an accurate color representation for a physical environment, but also to accurately capture color, lighting, and shadowing conditions in a live camera view, an image, or a video captured by a camera 1124. For example, the light/color sensor 1106 is applicable to determine when a color is captured required post-capture processing to provide better shading, brightness, hue, or other aspects, than is presently in an image capture frame.

In an implementation, any pair of cameras 1106 (in FIG. 11) that have at least a partially overlapping field of view, is used to provide 3D imaging by capturing image data for one or more objects from two different perspectives or points of view, and combining the information to produce a 3D image. Such processes are useful in the above embodiments, where the deeper color information is desired for different angles than a 2D view point. Example approaches include calculating an amount of disparity through a process such as edge matching, feature location and matching, color matching, and/or texture matching, and combining the disparity information with color information from each perspective to generate a three-dimensional image, either before or at a time of display. For example, if the image data is matched then the image data can be combined and/or displayed directly on a 3D-capable display, where the human brain can effectively do at least some of the 3D processing. In other examples, the image data can be otherwise combined or processed at the time of display such that upon displaying the image data, a 3D image is generated. A person of ordinary skill would recognize, with the present disclosure, that 3D image data can be used for other purposes or for further processing, such that using the image data to generate and display a 3D image is not required. For example, the image data can be used to determine shape and/or relative position information for various computer vision techniques, such as for determining one or more viewpoint and scale invariant feature information used for object recognition and/or tracking. For the computer vision techniques above, a computer vision engine of processor 1112 is applicable to decrease the burden on the processor 1112 by executing specific algorithms as detailed above.

In a further example implementation, motion sensor 1106 is configured to provide motion input to the UI using a user's face (e.g., eyes) to determine various aspects useful for determining relative orientation. The front camera includes, in an example, the features for the motion sensor 1106 to track a user's eye. Once the user's eye is tracked, an algorithm is processed to place a virtual box around an object of the representations of the objects in the screen view. The position and/or size of this box is continually updated and monitored in order to monitor relative user position. Similar algorithms can also be used to determine an approximate location and area of each of the user's eyes (or in some cases the eyes in tandem). In determining the location of the user's eyes, the processor 1112 can determine the view position of the user's head, and can determine that the user is facing the device. Further, the relative movement of the user's eyes can be easier to detect than the overall movement of the user's head when performing motions such as nodding or shaking the head back and forth. Monitoring the virtual box size also helps to provide distance information as well as directional information, which can be helpful when generating a 3D version of the captured image, live camera view, or video.

Once the positions of facial features of a user are identified, relative motion between the user and the device can be detected and utilized as input. For example, the UI of the above embodiments interfaces with the computing device and the movement of the user's head in an up and down movement, with respect to the viewable area of the image capture element, e.g., front facing camera 1102. As discussed, this could be the result of the user moving his or her head, side to side, or the user moving the device up and down (and further, side to side). Each of these movements are tracked, in an example, as a vertical or horizontal movement, respectively, and each can be treated differently as an input to provide a realistic view point for the live camera view, image, or video. As should be understood, such a process also can detect diagonal or other such movements. Further, the computing device, with the present disclosure, can also distinguish between different users using the eye information, at least.

As mentioned, various embodiments include tracking of one or more objects of interest in three-dimensional space. With the third dimension image data, i.e., depth, distance, or disparity, from at least a pair of 2D images, object tracking can be less sensitive to factors such as shadows, lighting changes, and camera dynamics. Depth, disparity, or distance information can also optimize object tracking. As the relative sizes of an object's features are known, the computational expense of searching over scales can be minimized and the probability of false detections may be reduced since the search space is decreased. Depth, distance, or disparity, in an example, is applied to obtain shape and size information that can help to differentiate among foreground objects for improved tracking. Further, the previously described occlusions is more easily detected and handled more explicitly when more 3D information is available. Depth, distance, or disparity also provides at least another disambiguating dimension that can help to improved tracking.

In some embodiments, determining, for a pixel, the closest color among the fine color representative is performed in a color space other than RGB space or HSV space. For example, Lab color space (CIELAB), which incorporates a dimension L for lightness and 'a' and 'b' for color-opponent dimensions could also be used for assigning pixels in an image to the fine color representatives. As used herein, a color opponent is associated with a process in color theory that suggests that color perception is controlled by the activity of two opponent systems: a blue-yellow mechanism and a red-green mechanism. Thus, the HSV space and Lab color space can be used for different purposes. For example, the HSV space can be used to determine the fine colors representatives and the Lab color space can be used to compute distances when comparing the color content of two images.

For example, for an image of a multi-colored shoe that includes equal parts of the color white and the color pink, the color information for the image can describe a histogram that generally represents equal parts of the colors white and pink. A comparison of the color information against a sample image for the color pink will typically generate a high visual similarity score. In addition, a comparison of the color information against a sample image for the color white will also generate a high visual similarity score. Thus, the colors white and pink can be selected as colors that are visually similar to the colors in the image of the multi-colored shoe.

Methods for capturing images or video using a camera element with a computing device are well known in the art and will not be discussed herein in detail. It is readily apparent, on reading the present disclosure, that image capture can be performed using a single image, multiple images, periodic imaging, continuous image capturing, image streaming, etc. Further, a device can include the ability to start and/or stop image capture, such as when receiving a command from a user, application, or other device. The example device similarly includes at least one audio capture component, such as a mono or stereo microphone or microphone array, operable to capture audio information from at least one primary direction. A microphone can be a uni-or omni-directional microphone as known for such devices.

As an example, a computing device can capture and/or track information for a user over a period of time. This information can include any appropriate information, such as location, actions (e.g., sending a message or creating a document), user behavior (e.g., how often a user performs a task, the amount of time a user spends on a task, the ways in which a user navigates through an interface, etc.), user preferences (e.g., how a user likes to receive information), open applications, submitted requests, received calls, and the like. As discussed above, the information can be stored in such a way that the information is linked or otherwise associated whereby a user can access the information using any appropriate dimension or group of dimensions.

The various embodiments can be implemented in a wide variety of operating environments, which in some cases can include one or more user computers, computing devices, or processing devices which can be used to operate any of a number of applications. User or client devices can include any of a number of general purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Various aspects also can be implemented as part of at least one service or Web service, such as may be part of a service-oriented architecture. Services such as Web services can communicate using any appropriate type of messaging, such as by using messages in extensible markup language (XML) format and exchanged using an appropriate protocol such as SOAP (derived from the "Simple Object Access Protocol"). Processes provided or executed by such services can be written in any appropriate language, such as the Web Services Description Language (WSDL). Using a language such as WSDL allows for functionality such as the automated generation of client-side code in various SOAP frameworks.

Most embodiments utilize at least one network that would be familiar to those skilled in the art for supporting communications using any of a variety of commercially-available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In embodiments utilizing a Web server, the Web server can run any of a variety of server or mid-tier applications, including HTTP servers, FTP servers, CGI servers, data servers, Java servers, and business map servers. The server (s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of databases and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A system comprising:
   a processor;
   a screen;
   a camera; and
   memory including instructions that, when executed by the processor, cause the system to:
      receive image data of a live camera view from the camera, the image data including representations of a physical environment;
      determine planes and surfaces from a representation of the representations;
      analyze the planes and the surfaces using relative measurements between the planes and the surfaces to obtain shapes and depth information for available spaces within the physical environment;
      determine locations of the camera with respect to the physical environment for different portions of the image data;
      analyze the shapes and the depth information using a trained neural network which determines types of items fitting the available spaces, based on a type of the physical environment;
      overlay the live camera view with a selection from the types of items to provide an augmented reality (AR) view of the physical environment from an individual location of the locations, the selection from the types of items being fixed in position in the AR view to at least one of the planes or at least one of the surfaces, with respect to one or more virtual anchor points presented in the AR view;
      allow movement through the AR view to a different location than the individual location by an input received indicating a selected virtual anchor point of the one or more virtual anchor points presented in the AR view while the selection from the items remains anchored to the individual location, the selected virtual anchor point determined using at least the planes and the surfaces.

2. The system of claim 1, wherein the instructions when executed by the processor further enable the system to:
   determine categories for the items, the categories comprising one or more of dimensions, weight, color, shape, texture, material, and size;
   provide the categories to the screen; and
   provide the selection from the items based in part on a category selection from the categories.

3. The system of claim 1, wherein the instructions when executed by the processor further enable the system to:

provide one or more of:
  a selectable option to procure the selection from the items via an electronic marketplace;
  information associated with the selection from the items;
  advertisement associated with the selection from the items; and
  location information associated with stores that provide the selection from the items.

4. The system of claim 1, wherein the instructions when executed by the processor further enable the system to:
  store the image data along with the planes, the surfaces, and the locations;
  receive a request to review items in the representation;
  receive an input for adjusting a zoom or adjusting a location in the augmented reality view, the adjusting a zoom or the adjusting the location by selecting a portion of the representation;
  update the image data to the portion of the representation, the update to the image data including a change in the items for the representation.

5. The system of claim 1, wherein the instructions when executed by the processor further enable the system to:
  assign a value to the planes and the surfaces of the representation;
  determine categories for the items;
  compare the value with stored values that are associated with one or more of: the categories for the items and the items, from a database, to determine visual similarity scores between the stored values and one or more of: the categories and the items;
  determine that a visual similarity score of the visual similarity scores satisfies a threshold; and
  determine the selection from the items based in part on the visual similarity score.

6. The system of claim 5, wherein the instructions when executed by the processor further enable the system to:
  generate a slider that is configured to adjust the value associated with the planes and the surfaces of the representation;
  receive an adjustment of the slider;
  adjust the value to generate an updated value, wherein the updated value is associated with a new item from the items.

7. A computer-implemented method comprising:
  receiving image data of a live camera view from the camera, the image data including representations of a physical environment;
  analyzing the image data to obtain shapes and depth information of the physical environment, based at least in part on measurement data associated with planes and one or more surfaces detected in the image data;
  generating items, determined by a trained neural network, associated with the shapes and depth information of the physical environment and based on a type of the physical environment;
  overlaying the items in the representation to provide an augmented reality (AR) view of the physical environment, the items being fixed in position in the AR view to at least one of the planes or at least one of the surfaces, with respect to one or more virtual anchor points presented in the AR view; and
  allowing movement through the AR view from the representation to a new representation by an input received indicating a selected virtual anchor point of the one or more virtual anchor points presented in the AR view while maintaining the items in a fixed position relative to the representation, the selected virtual anchor point determined using at least the planes and the surfaces.

8. The computer-implemented method of claim 7, further comprising:
  receiving a selection of an edge in the representation, the selection of an edge defining adjacent planes in the representation;
  receiving a selection of one or more surfaces in the representation;
  receiving location information associated with the camera during the capture of the image data;
  associating the location information with the planes and the one or more surfaces; and
  providing, as part of the augmented reality view, items associated with the planes and the one or more surfaces.

9. The computer-implemented method of claim 7, further comprising:
  receiving a floor layout of the physical environment as part of the image data;
  receiving a first selection for edges in the representation, the selection of the edges separating adjacent planes in the representation;
  receiving a second selection that defines surfaces in the physical environment;
  receiving a third selection of a location in the floor layout;
  receiving, from different directions of the camera at the location, portions of the image data;
  associating an individual direction of the different directions and the location with the portions of the image data; and
  storing the image data with the planes, the edges, the surfaces, the location, and the different directions for further processing in the augmented reality view.

10. The computer-implemented method of claim 7, further comprising:
  generating categories of items associated with the shapes and depth information of the physical environment;
  receiving one or more selections from the categories of items; and
  generating the items associated with the one or more selections.

11. The computer-implemented method of claim 10, wherein the items are ranked in accordance with a popularity measure from prior sales of the items through an electronic marketplace.

12. The computer-implemented method of claim 7, wherein an item of the items corresponds to a sponsored item, provided by a curator or an item sponsor, for inclusion in the augmented reality view.

13. The computer-implemented method of claim 7, wherein an item of the items corresponds to one of a brand of product preferred by a user, a complementary item from the representation, or a contrasting item for the representation.

14. The computer-implemented method of claim 7, further comprising:
  determining that an additional edge is associated to the edges from the first selection using mapping data from one or more locations associated with the camera;
  determining that additional planes associated to the additional edge is also associated with the edges from the first selection; and
  augmenting the augmented reality view to include the additional planes.

15. The computer-implemented method of claim 14, wherein the augmenting of the augmented reality view provides a panoramic view by stitching together the additional planes to the planes associated with the edges from the first selection.

16. The computer-implemented method of claim 14, wherein the augmenting of the augmented reality view provides a timeline view of changes to the representation by the additional planes associated to the planes, the timeline view relying on time information associated with the image data and with additional image data associated with the additional planes.

17. The computer-implemented method of claim 14, wherein the additional edge and the additional planes are associated with later or prior image data than the image data.

18. The computer-implemented method of claim 7, further comprising:
 saving the live camera view as an original version and the augmented reality view as an augmented version; and
 displaying the original version and the augmented version, either concurrently or separately.

19. A non-transitory computer-readable storage medium including instructions that, when executed by at least one processor, cause the at least one processor to:
 receive image data of a live camera view from the camera, the image data including a representation of a physical environment;
 analyze the image data to obtain shapes and depth information of the physical environment, based at least in part on measurement data associated with planes and one or more surfaces detected in the image data;
 generate items, determined by a trained neural network, associated with the shapes and depth information of the physical environment, and based on a type of the physical environment;
 overlay the items in the representation to provide an augmented reality (AR) view of the physical environment, the items being fixed in position in the AR view to at least one of the planes or at least one of the surfaces, with respect to one or more virtual anchor points presented in the AR view; and
 allow movement through the AR view from the representation to a new representation by an input received indicating a selected virtual anchor point of the one or more virtual anchor points presented in the AR view while maintaining the items in a fixed position relative to the representation, the selected virtual anchor point determined using at least the planes and the surfaces.

20. The non-transitory computer-readable storage medium of claim 19, wherein the instructions when executed further cause the at least one processor to:
 receive a floor layout of the physical environment as part of the image data;
 receive a first selection for edges in the representation, the selection of the edges separating adjacent planes in the representation;
 receive a second selection that defines surfaces in the physical environment;
 receive a third selection of a location in the floor layout;
 receive, from different directions of the camera at the location, portions of the image data;
 associate an individual direction of the different directions and the location with the portions of the image data; and
 store the image data with the planes, the edges, the surfaces, the location, and the different directions for further processing in the augmented reality view.

\* \* \* \* \*